US012600734B2

(12) United States Patent
Okamoto et al.

(10) Patent No.: US 12,600,734 B2
(45) Date of Patent: Apr. 14, 2026

(54) PHOTOSENSITIZING DYE

(71) Applicants: The University of Tokyo, Tokyo (JP); PhotoQ3 Inc., Tokyo (JP)

(72) Inventors: Akimitsu Okamoto, Tokyo (JP); Wakako Dewa, Tokyo (JP); Takao Hamakubo, Tokyo (JP); Mikako Hamabe, Tokyo (JP); Naoko Toda, Tokyo (JP); Yukio Sudo, Tokyo (JP)

(73) Assignees: THE UNIVERSITY OF TOKYO, Tokyo (JP); PHOTOQ3 INC., Tokyo (JP)

( * ) Notice: Subject to any disclaimer, the term of this patent is extended or adjusted under 35 U.S.C. 154(b) by 625 days.

(21) Appl. No.: 18/012,050

(22) PCT Filed: Jun. 24, 2021

(86) PCT No.: PCT/JP2021/023911

§ 371 (c)(1),
(2) Date: Dec. 21, 2022

(87) PCT Pub. No.: WO2021/261546

PCT Pub. Date: Dec. 30, 2021

(65) Prior Publication Data

US 2023/0242554 A1 Aug. 3, 2023

(30) Foreign Application Priority Data

Jun. 24, 2020 (JP) ................................ 2020-108318

(51) Int. Cl.

| | |
|---|---|
| ***C07F 3/06*** | (2006.01) |
| ***A61K 41/00*** | (2020.01) |
| ***A61K 47/68*** | (2017.01) |

(52) U.S. Cl.

CPC ............ *C07F 3/06* (2013.01); *A61K 41/0057* (2013.01); *A61K 47/6803* (2017.08)

(58) Field of Classification Search

CPC .... C07F 3/06; A61K 41/0057; A61K 47/6803
See application file for complete search history.

(56) References Cited

U.S. PATENT DOCUMENTS 5,124,067 A * 6/1992 Itoh ...................... C07D 487/22 252/299.61

FOREIGN PATENT DOCUMENTS

| | | | | |
|---|---|---|---|---|
| JP | 9-501928 A | 2/1997 | | |
| JP | 2004-529171 A | 9/2004 | | |
| WO | 95/05818 A1 | 2/1995 | | |
| WO | 02/090361 A1 | 11/2002 | | |
| WO | WO-02096913 A1 * | 12/2002 | ............. | A61P 43/00 |
| WO | WO-2004020529 A1 * | 3/2004 | ............ | B29C 66/71 |

OTHER PUBLICATIONS

Furuyama, T. et al., "Cationic axial ligands on sulfur substituted silicon(iv) phthalocyanines: improved hydrophilicity and exceptional red-shifted absorption into the NIR region", Chem Comm., vol. 55, 2019, pp. 7311-7314.

Drechsler, U. et al., "Synthesis of Novel Functionalised Zinc Phthalocyanines Applicable in Photodynamic Therapy", Eur. J. Org. Chem., No. 12, 1999, pp. 3441-3453.

(Continued)

*Primary Examiner* — Jeffrey S Lundgren
*Assistant Examiner* — W. Justin Youngblood
(74) *Attorney, Agent, or Firm* — Greenblum & Bernstein, P.L.C.

(57) ABSTRACT

It is an object of the present invention to provide a compound that has absorption in a near infrared region, has high efficiency of singlet oxygen generation (quantum yield), and also has high tumor toxicity when it is combined with an immunotoxin. According to the present invention, provided is a compound represented by the following formula (1) or a salt thereof:

(I)

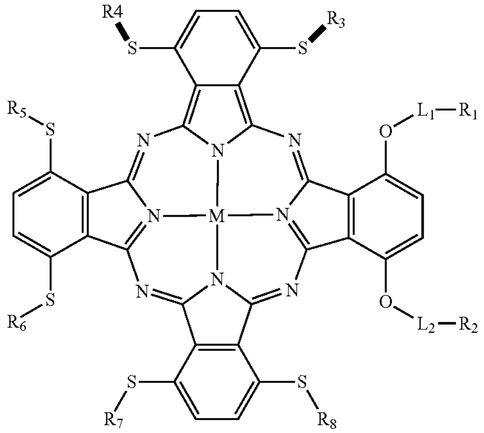

wherein $L_1$ and $L_2$ each independently represent a single bond, —O—, —CO—, an alkylene group containing 1 to 8 carbon atoms, a sugar chain, or a combination thereof; $R_1$ and $R_2$ each independently represent an alkyl group containing 1 to 8 carbon atoms, a carboxylic acid group, an amino group, a hydroxyl group, a thiol group, or a biotin residue; $R_3$, $R_4$, $R_5$, $R_6$, $R_7$ and $R_8$ each independently represent an alkyl group containing 1 to 8 carbon atoms, a phenyl group, a carboxylic acid group, an amino group, a hydroxyl group, a thiol group, or a biotin residue; and M represents Mg, Zn, Fe, P, Si, Cu, Sn, Al, Ti, Mo, or Ni.

15 Claims, 12 Drawing Sheets

(56) References Cited

OTHER PUBLICATIONS

International Search Report and Written Opinion of the International Searching Authority issued in International Patent Application No. PCT/JP2021/023911, dated Aug. 10, 2021, along with an English translation thereof.
International Preliminary Report on Patentability issued in International Patent Application No. PCT/JP2021/023911, dated Dec. 13, 2022, along with an English translation thereof.
Extended European Search Report that issued in corresponding European patent application No. 21828864.5, dated Aug. 7, 2024.

* cited by examiner

[Fig. 1]
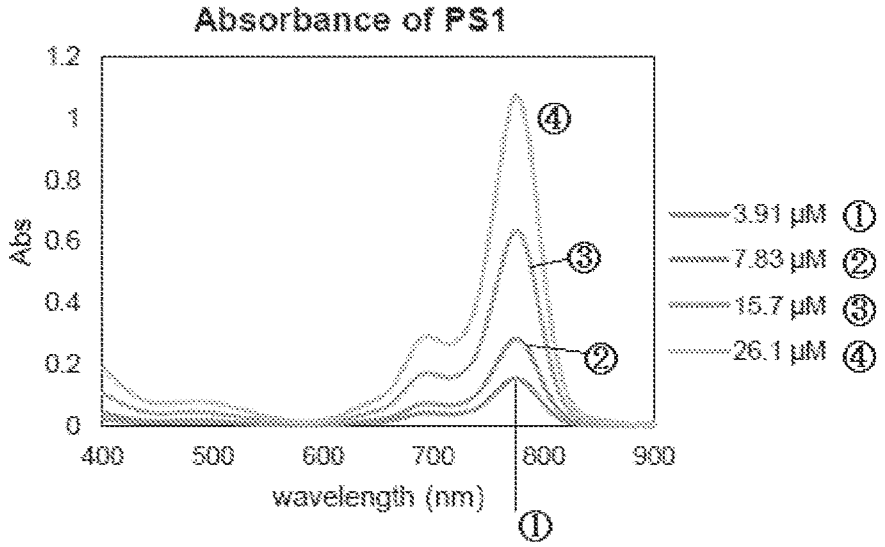
[Fig. 2]
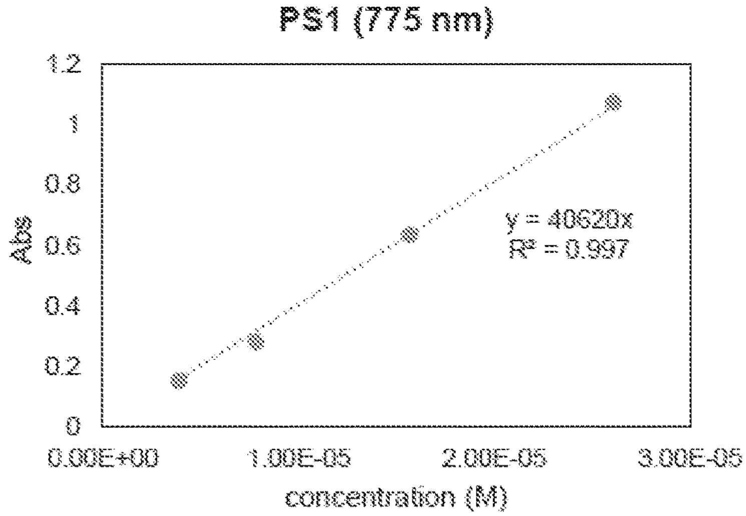

[Fig. 3]
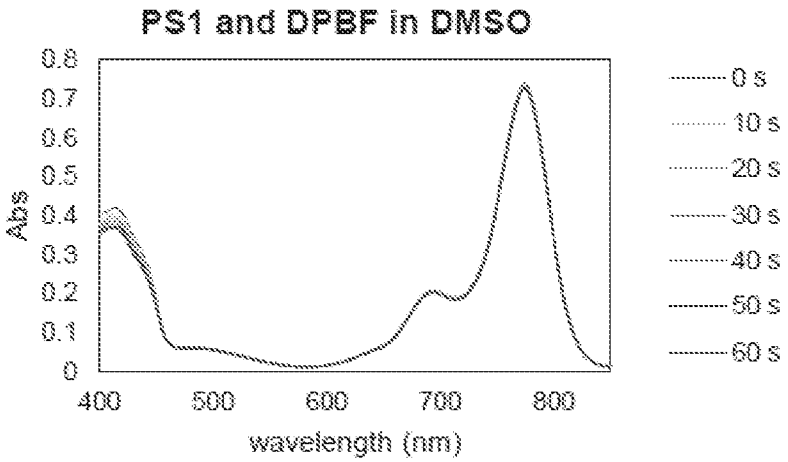
[Fig. 4]
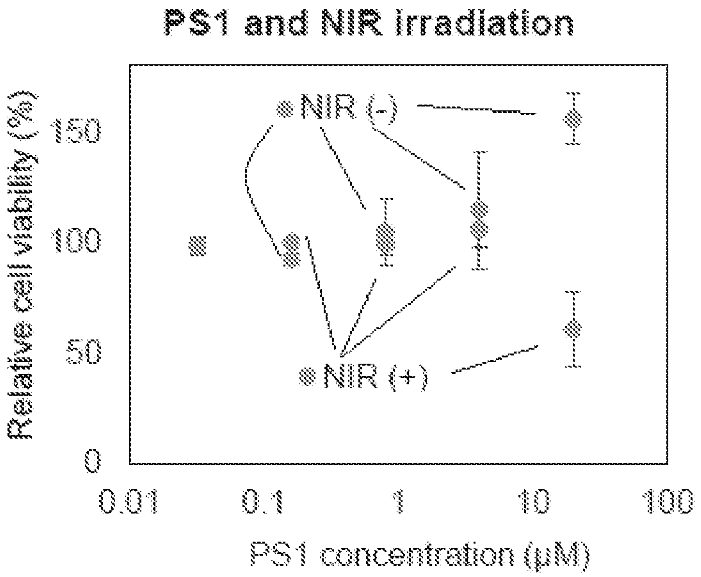

[Fig. 5]
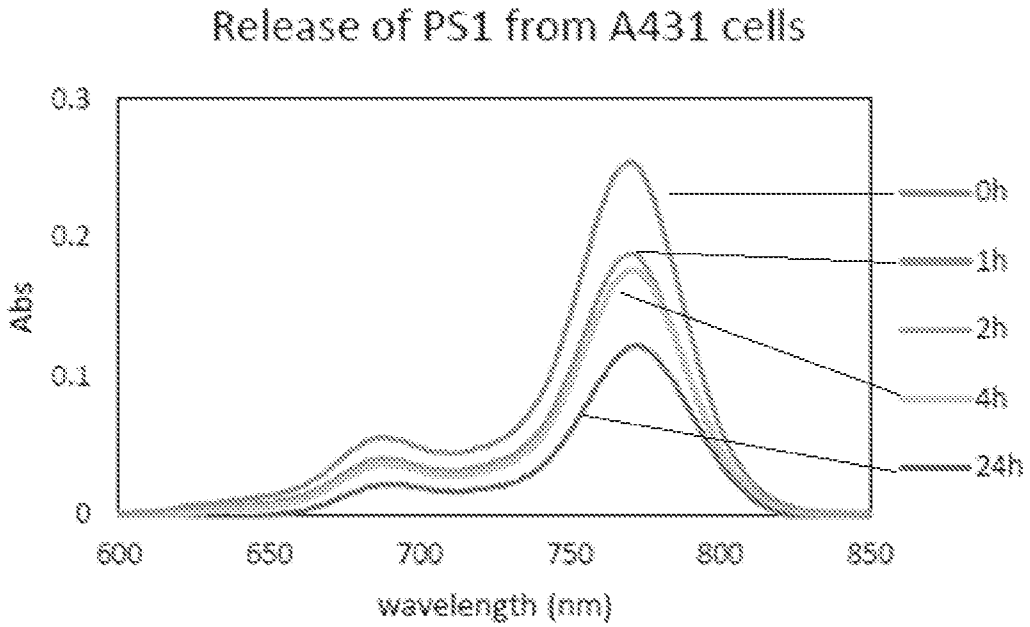
[Fig. 6]
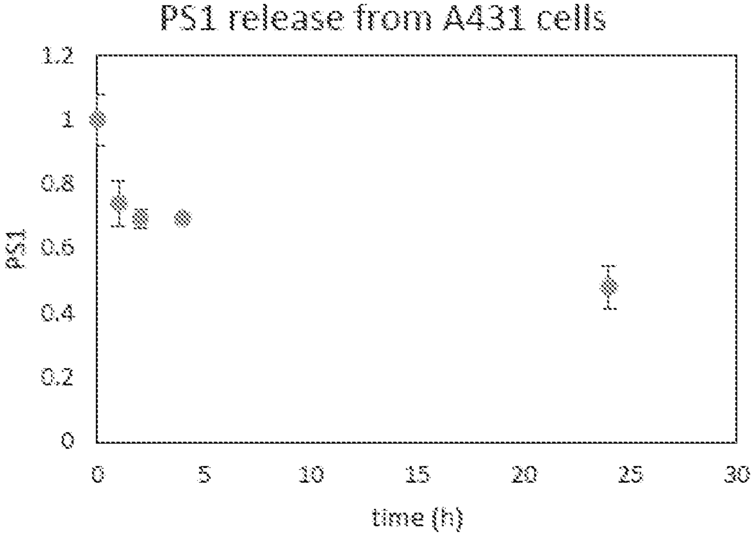

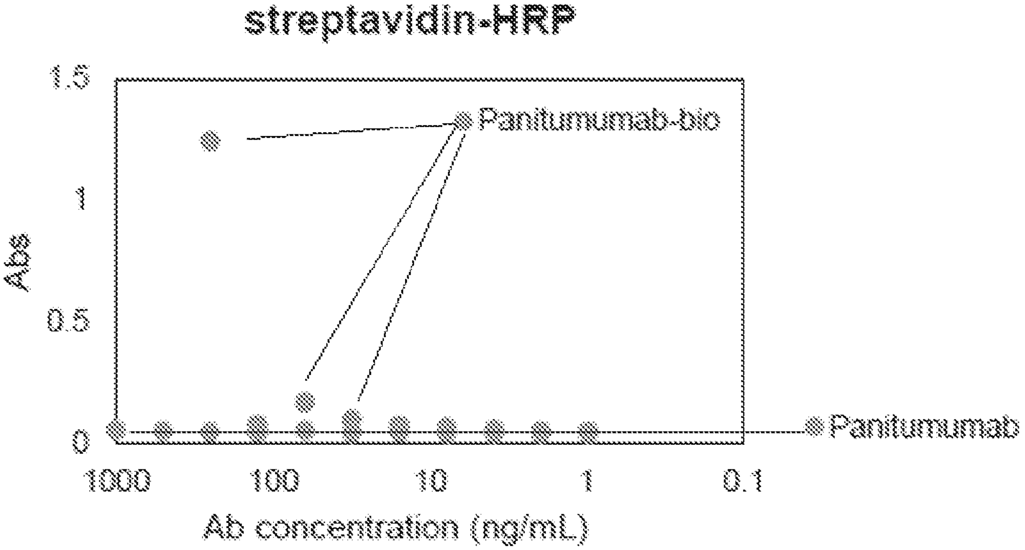
[Fig. 7]
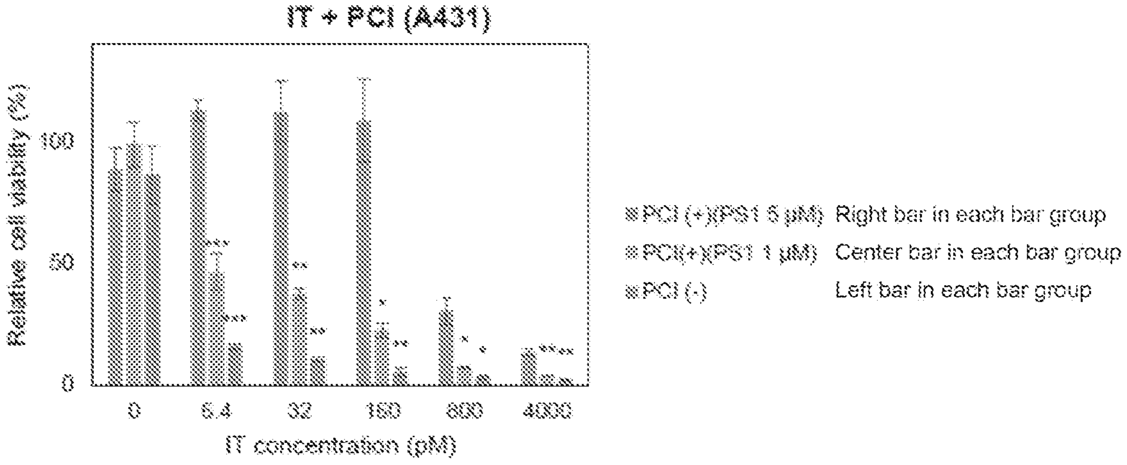
[Fig. 8]
PCI (+)(PS1 5 µM)  Right bar in each bar group
PCI(+)(PS1 1 µM)  Center bar in each bar group
PCI (-)           Left bar in each bar group

[Fig. 9]
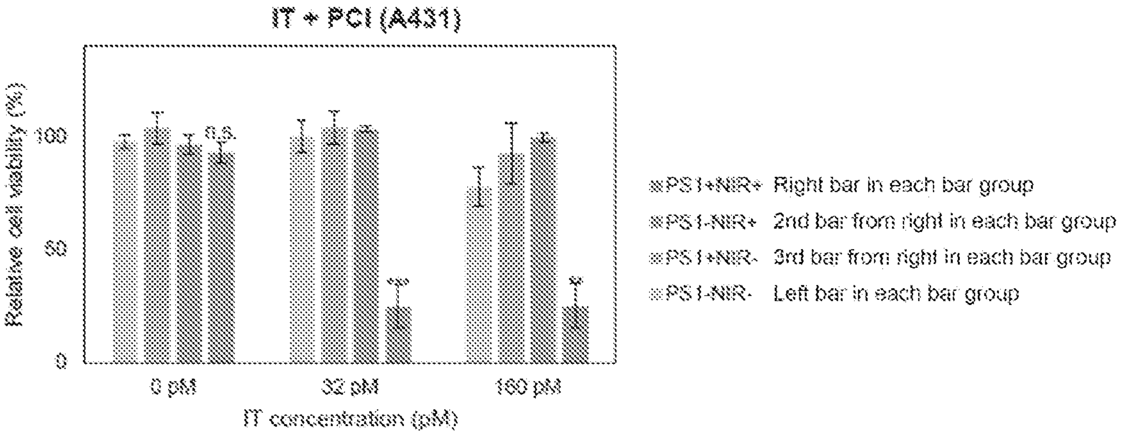
[Fig. 10]
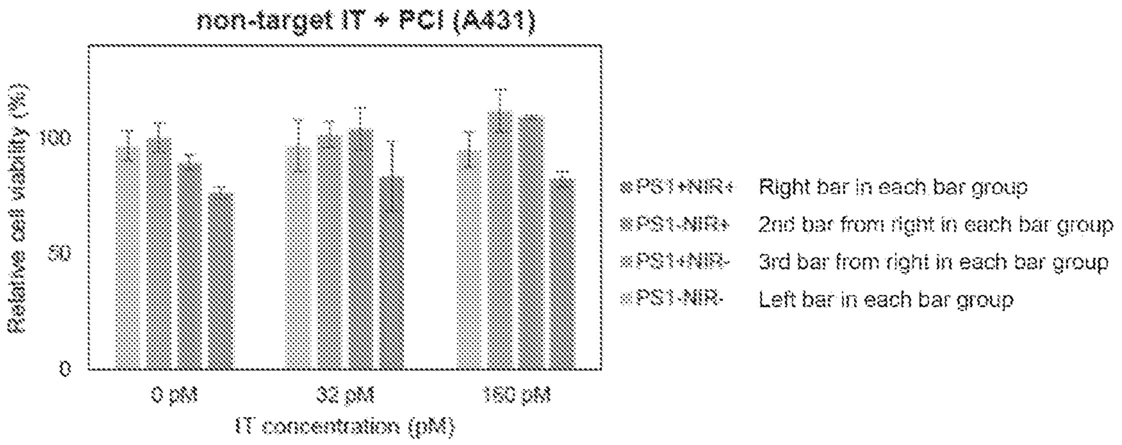

[Fig. 11]
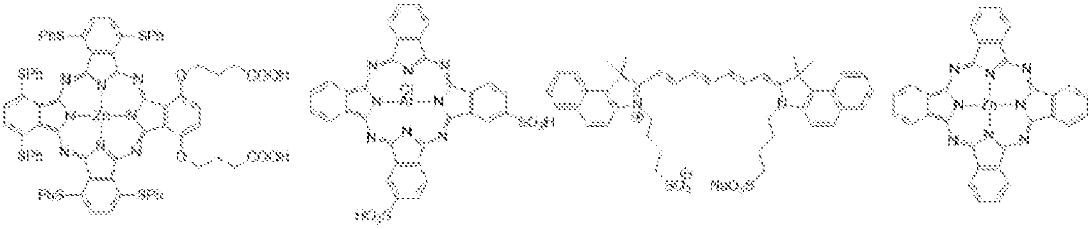
| PS1 | AlPcS2a | Indocyanine green (ICG) | Zinc phthalocyanine (ZnPc) |
|---|---|---|---|
| $\lambda_{ab}$ = 775 nm | $\lambda_{ab}$ = 677 nm | $\lambda_{ab}$ = 795 nm | $\lambda_{ab}$ = 672 nm |
| $\Phi_{\Delta}$ = 0.61 | $\Phi_{\Delta}$ = 0.17[36] | $\Phi_{\Delta}$ = 0.12[37] | $\Phi_{\Delta}$ = 0.67[38] |
[Fig. 12]
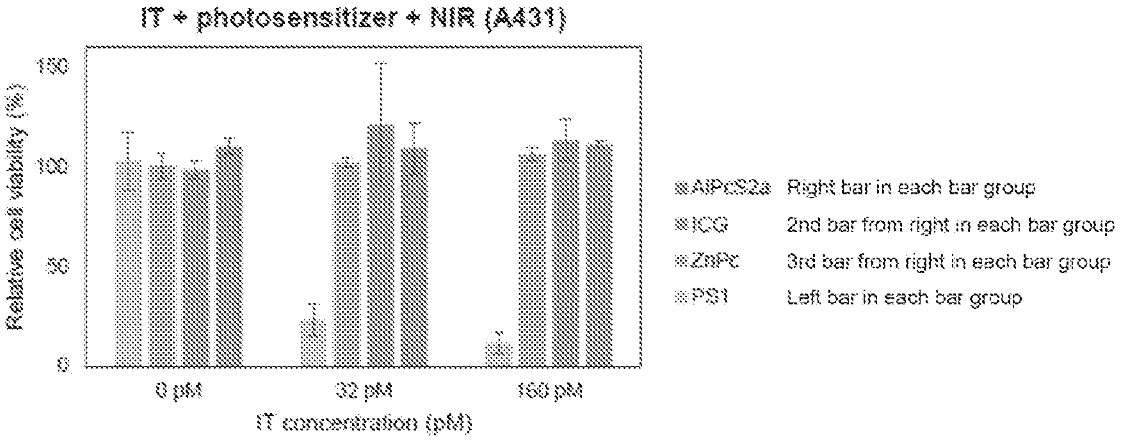

[Fig. 13]
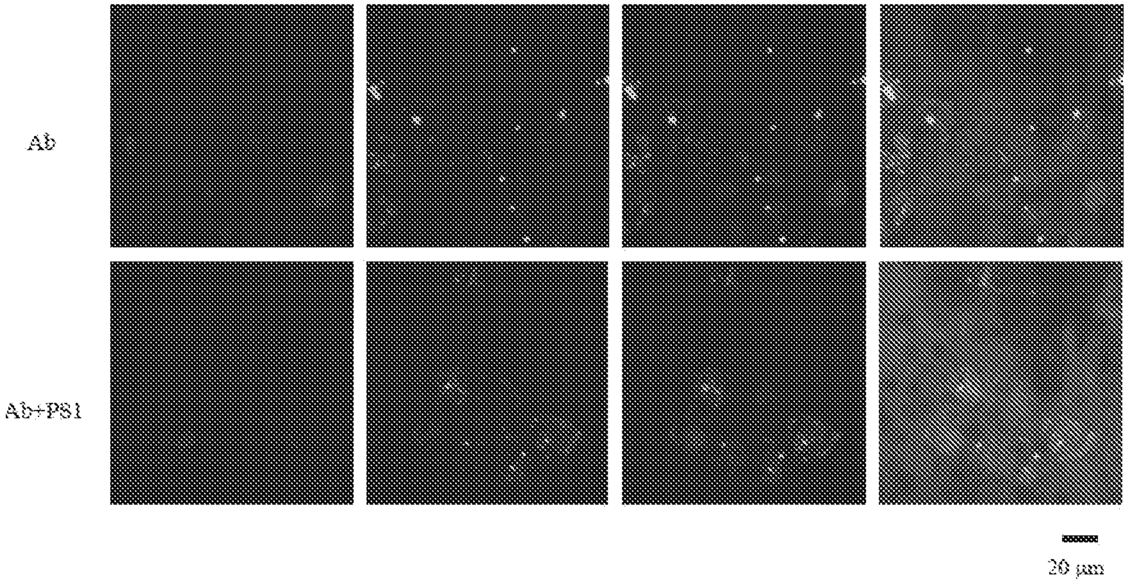
[Fig. 14]
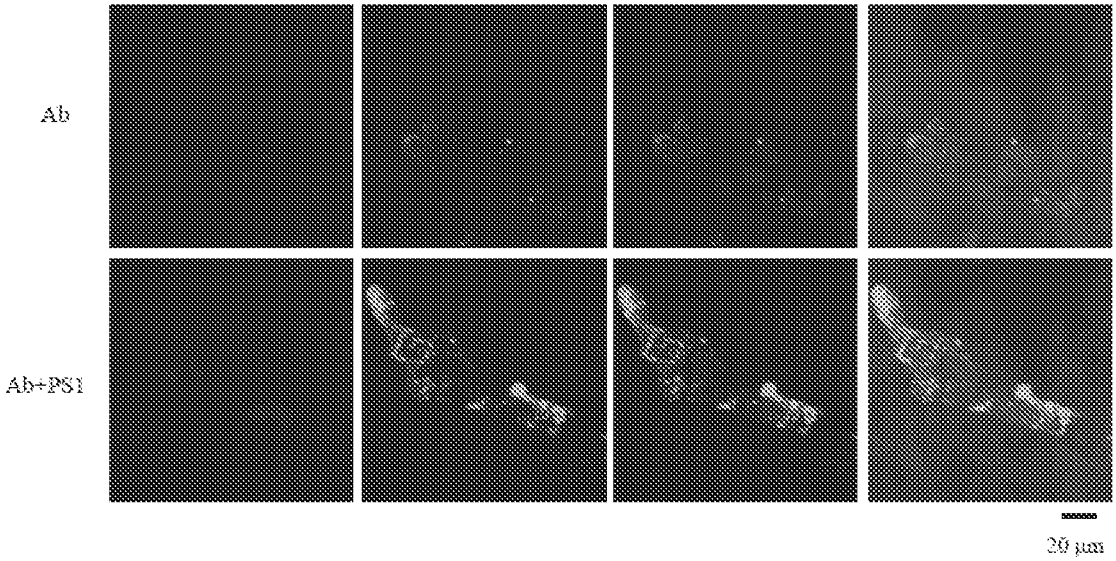

[Fig. 15]
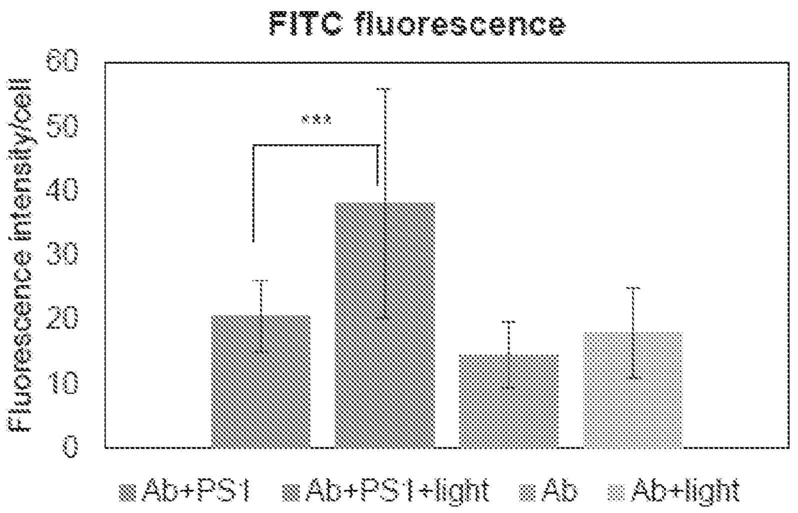
[Fig. 16]
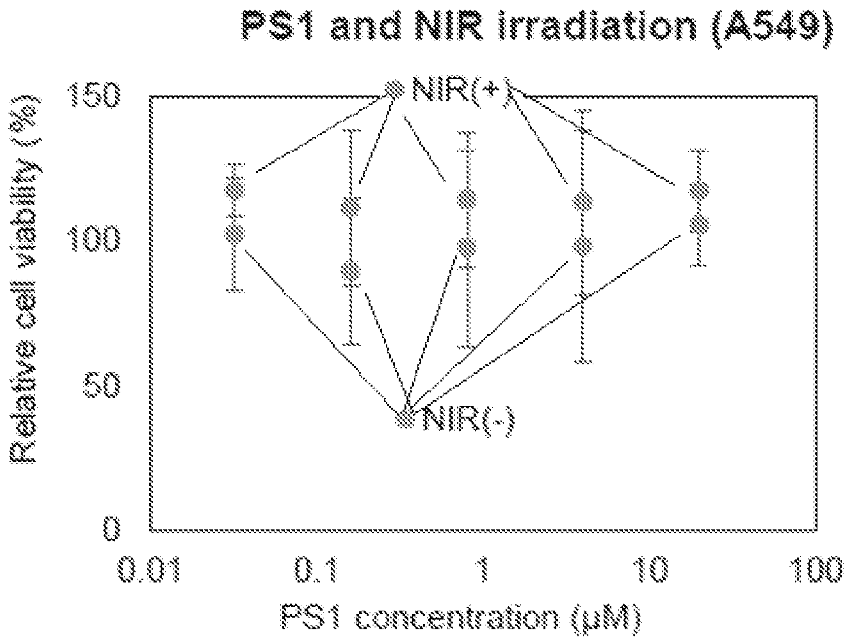

[Fig. 17]
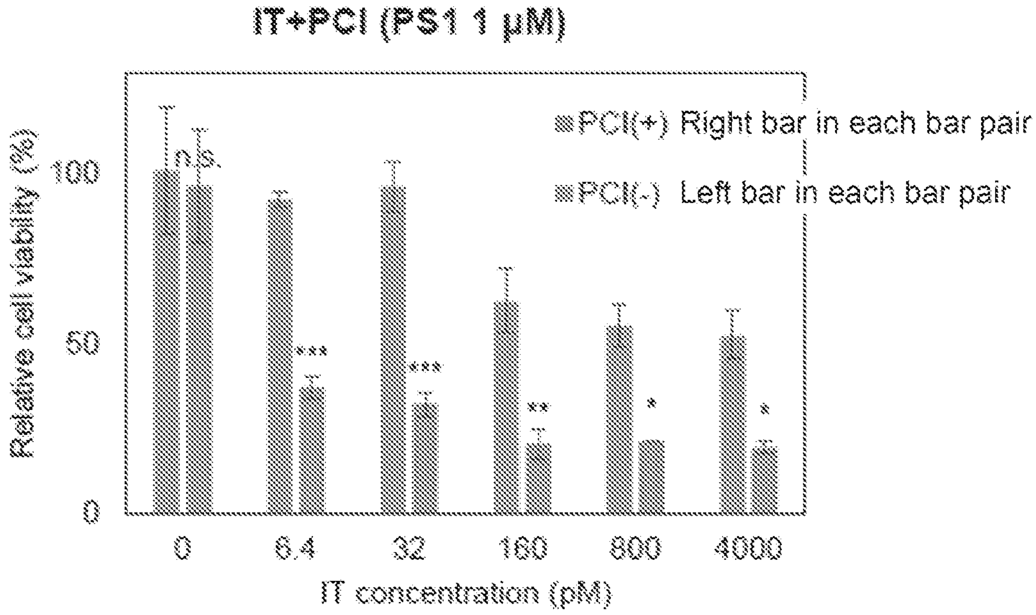
[Fig. 18]
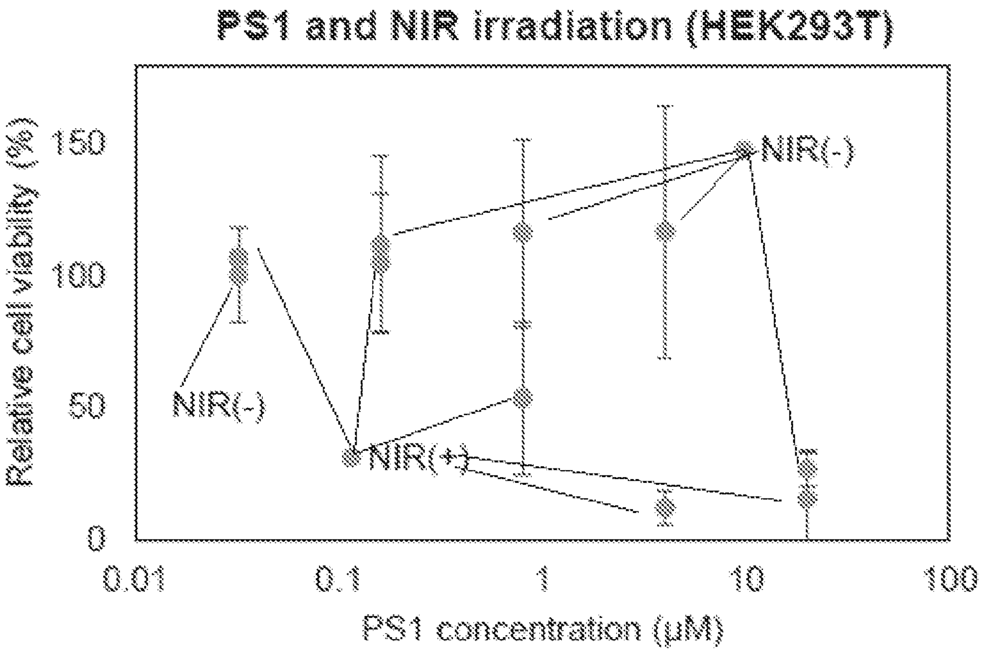

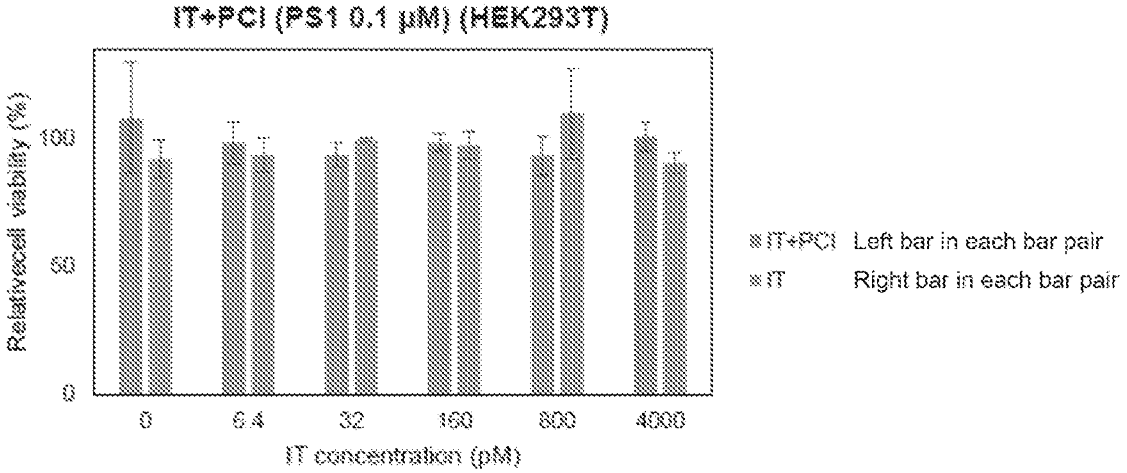
[Fig. 19]
IT+PCI (PS1 0.1 μM) (HEK293T)
※ IT+PCI   Left bar in each bar pair
※ IT      Right bar in each bar pair
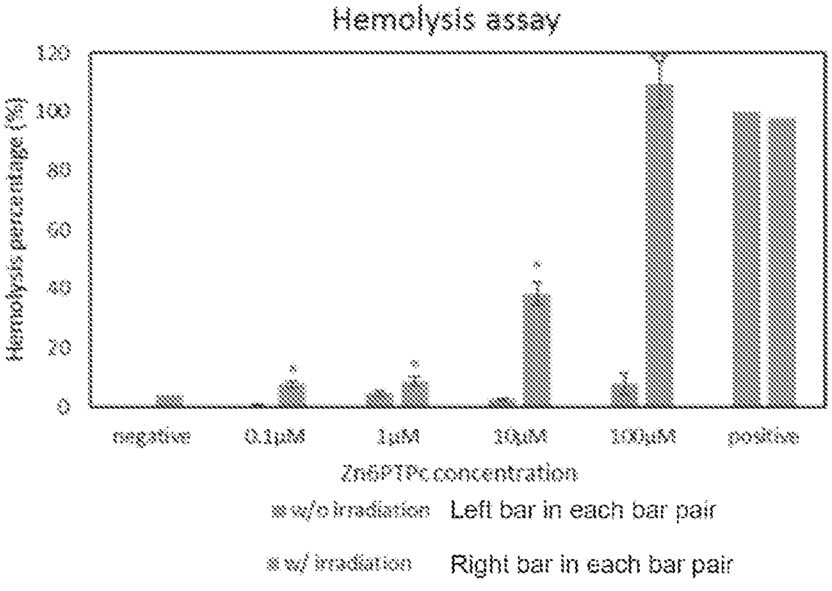
[Fig. 20]
Hemolysis assay
※ w/o irradiation   Left bar in each bar pair
※ w/ irradiation   Right bar in each bar pair

[Fig. 21]
(a)
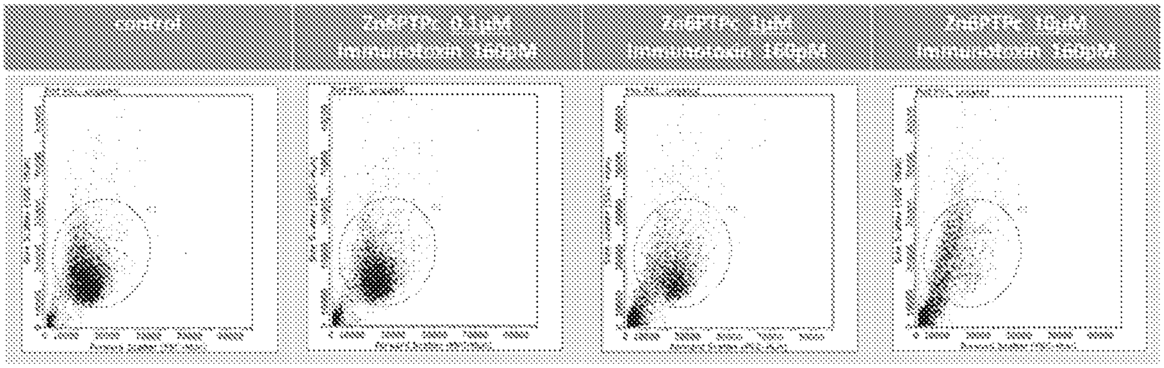
(b)
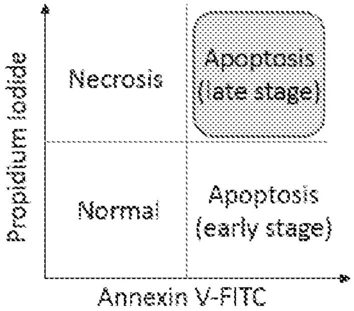
(c)
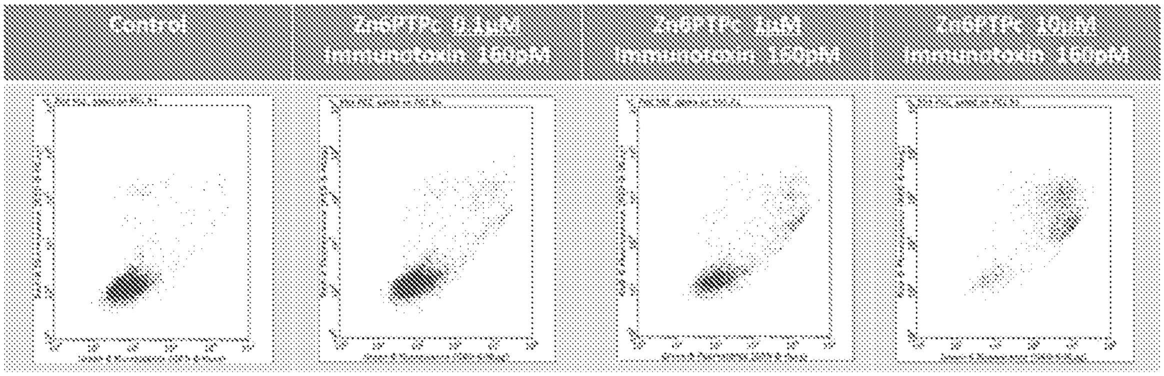

[Fig. 22]
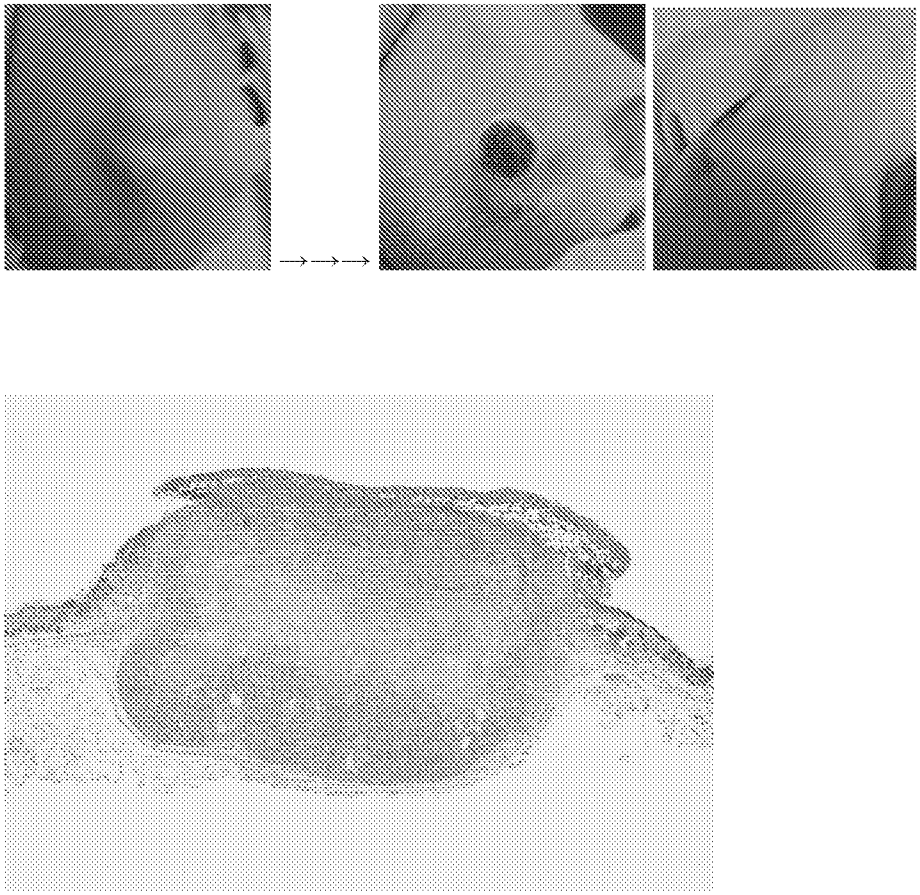

PHOTOSENSITIZING DYE

TECHNICAL FIELD

The present invention relates to a novel photosensitizing dye useful for killing tumor cells, and utilization thereof.

BACKGROUND ART

At present, main therapeutic methods for cancer are surgery, anticancer drug therapy, and radiation therapy. All of these therapeutic methods are attended with pain and side effects, and a heavy burden is imposed on the body of patients. A photo dynamic therapy has attracted attention as a therapeutic method that reduces such burden on patients. The photo dynamic therapy is a therapeutic method, which comprises administering a photosensitizer into the body of a patient so that the photosensitizer is allowed to accumulate in tumor cells, then applying a near infrared light, at a pinpoint, to the tumor cells to generate singlet oxygen, and then killing the tumor cells by the cytotoxicity of the singlet oxygen. The photo dynamic therapy is greatly advantageous in that this therapy is able to treat a focus of disease, to which surgery cannot be applied, and in that this therapy has almost no such side effects as those caused by anticancer drugs. On the other hand, the photo dynamic therapy also has several disadvantages that hinder the widening of the range of practical application thereof. One of such disadvantages is a problem regarding photosensitizers. Examples of the photosensitizers used in the photo dynamic therapy may include photofrin, laserphyrin, indocyanine green, and 5-aminolevulinic acid (5-ALA). However, the absorption maximums of photofrin (λab=630 nm), laserphyrin (λab=664 nm), and 5-ALA (in the case of protoporphyrin IX generated as a result of metabolizing 5-ALA in the cytoplasm, λab=405 nm) are all present in the visible light region (Non-Patent Documents 1 and 2). Since the biopermeability of a visible light is inferior to that of a near infrared light, these photosensitizers are not suitable for the treatment of a focus of disease present in the deep part of a body. On the other hand, the absorption maximum of indocyanine green (λab=800 nm) is present in the near infrared region. However, indocyanine green is poor in terms of chemical stability because it has a long unsaturated carbon chain. Indocyanine green is decomposed in several tens of seconds as a result of light irradiation, and it becomes unfunctional as a photosensitizer (Non-Patent Document 3).

Another disadvantage of the photo dynamic therapy is that the accumulation ability of photosensitizers to specifically accumulate in tumor cells is low. Although the accurate mechanisms of porphyrins such as photofrin and laserphyrin have not been elucidated, these photosensitizers have been known to accumulate in tumors. Moreover, regarding indocyanine green, studies have been conducted to bind indocyanine green to a liposome, or to bind indocyanine green to a polymer to form nanoparticles, so that the molecular size of indocyanine green is increased, and the efficiency of incorporating it into a tumor is improved as a result of an EPR effect (Non-Patent Documents 4 and 5). The EPR effect is a property by which macromolecular drugs each having a size of several hundreds of nanometers are accumulated in a tumor due to the immature blood vessel structure thereof, whereas the incorporated drugs cannot be discharged to the outside of the tumor tissues due to immature lymphatic tissues, and as a result, the macromolecular drugs are accumulated in the tumor cells. However, a difference in the concentration of such a photosensitizer between in tumor cells and in normal cells is small, and thus, it cannot be said that the photosensitizer has sufficient specificity.

As mentioned above, the photo dynamic therapy has still had many problems. In recent years, however, novel therapeutic methods have been actively developed based on the photo dynamic therapy. One of such novel therapeutic methods is a photoimmunotherapy proposed by Hisataka KOBAYASHI et al., National Cancer Institute, USA (Non-Patent Document 6). The photoimmunotherapy is a photo dynamic therapy performed by allowing the photosensitizer IR700DX to bind to an antibody that binds to a protein specifically expressed in tumor cells. According to an antigen-antibody reaction, the ability of a drug to specifically accumulate in tumor cells is greatly enhanced, when compared with single administration of a photosensitizer. Cancer therapy using antibody drugs has been carried out since before. The action mechanism of such cancer therapy using antibody drugs is broadly divided into two types. That is, there are two types of activities, namely, ADCC activity, by which when antibodies bind to cells or pathogens, immune cells that recognize the Fc regions of the antibodies, such as macrophages or NK cells, are attracted, and the immune cells then kill the cells or pathogens to which the antibodies bind; and CDC activity, by which when complements bind to the Fc regions of antibodies that bind to target antigens, the activation reaction of the complements takes place as a chain reaction, and the finally formed complex dissolves the cell membrane. Furthermore, in order to enhance a tumor-killing ability, in addition to the aforementioned two activities, a treatment has also been carried out by using an anti-cancer agent-bound antibody (Non-Patent Document 7) or a radioactively labeled antibody (Non-Patent Document 8). However, these treatments have been problematic in that such an anti-cancer agent or a radioactive substance also gives damage to cells other than tumor cells. On the other hand, in the case of photoimmunotherapy, a site on which a drug acts can be double-restricted by accumulating photosensitizer-bound antibodies in tumor cells and then by applying a laser to the accumulated site. Thus, the photoimmunotherapy can be said to be a therapeutic method giving less damage to normal cells and having fewer side effects.

Another cancer therapeutic method is photochemical internalization (PCI). PCI is a drug delivery method for enhancing the endosomal escape efficiency of a drug (mainly, a biopolymer) by applying a photosensitizer and light irradiation, and this method has been proposed for the first time by Berg et al. in 1999 (Non-Patent Document 9). In general, biopolymers such as proteins or nucleic acids are first incorporated into cells through an endosomal pathway, and are then transferred into, mainly, a lysosomal degradation system. Accordingly, it has been difficult for such biopolymers to sufficiently exhibit their functions in cells. Thus, according to PCI, singlet oxygen generated by light irradiation to a photosensitizer destroys the endosomal membrane before biopolymers are transferred into the lysosome, and as a result, the biopolymers are released into the cytoplasm. Thereby, the biopolymers can exhibit their functions in cells without being decomposed. In 2016, a clinical experiment (phase 1) was carried out to enhance the medicinal effects of bleomycin as an anticancer agent by PCI using the photosensitizer TPCS2a. In this clinical experiment, tumors completely disappeared in 58% of patients, and tumors were reduced in 11% of patients (Non-Patent Document 10). As such, it is suggested that drugs that have not previously exhibited medicinal effects due to low endosomal escape efficiency are likely to provide sufficient therapeutic effects according to PCI.

Moreover, as another method, a method of combining a photosensitizer with a conjugate of a substance that binds to a target substance on the surface of tumor cells and a cytotoxin has been conceived. According to this method, a conjugate of a substance that binds to a target substance on the surface of tumor cells and a cytotoxin (e.g. an immunotoxin), which was internalized in the endosome of the tumor cell, can exhibit strong therapeutic effects, when a light is applied to the photosensitizer for its endosomal escape.

Near infrared light is a light having a wavelength of about 700 to 1500 nm, which is characterized in that absorption by water or hemoglobin or scattering due to biomolecules is small and biopermeability is high, in that the near infrared light has such low energy that it does not damage living bodies, in that its autofluorescence is small, and in that the near infrared light is useful for observation or regulation of living bodies. Hence, near infrared light-absorbing dyes have been utilized in various types of imaging (fluorescence, two-photon, and photoacoustic wave), the treatments of diseases (photo dynamic therapy and photothermal therapy), and the like. However, since there are only a few types of such near infrared light-absorbing dyes, the near infrared light-absorbing dyes have not yet been used in a wide range of applications.

When compared with many dyes that absorb an ultraviolet light and a visible light, the types of the near infrared light-absorbing dyes are limited to phthalocyanine, squaline, and some cyanine dyes. Some dyes have already been used to treat diseases in clinical sites. However, if considering application of these dyes to living bodies, the dyes have many problems. Phthalocyanine has properties by which it has low water-solubility and easily forms an aggregate in water. In order to solve such low water-solubility, many sulfo group-introduced phthalocyanines have been developed. However, since anionic substituents react against phosphoric acid groups on the cell membrane, they are hardly incorporated into cells (Non-Patent Document 11). Squaline has low water-solubility and also has a highly electrophilic cyclobutyl skeleton. Thus, squaline has high chemical reactivity and is likely to react with biomolecules (Non-Patent Document 12). Cyanine has a small Stokes shift and is easily influenced by a scattered light. In addition, since cyanine having a long absorption wavelength has a long unsaturated carbon chain, it lacks chemical stability (Non-Patent Document 13). Moreover, regarding all of these dyes, functionalization of the dyes directed towards achieving application thereof to living bodies has not been promoted. If such functionalization is carried out, the molecular size of the dyes is increased, and as a result, the biocompatibility of the dyes is further decreased. Taking into consideration these problems, it has been desired to develop a dye molecule that is suitable for application to living bodies and is capable of sufficiently exhibit the properties of a near infrared light-absorbing dye.

PRIOR ART DOCUMENTS

Non-Patent Documents

Non-Patent Document 1: H. Kataoka et al., Ann. Transl. Med., 2017, 5, 183

Non-Patent Document 2: T. J. Beck et al., J. Photochem. Photobiol., 2007, 87, 174

Non-Patent Document 3: M. Fuyuki et al., J. Photochem. Photobiol. A, 2013, 252, 152-158

Non-Patent Document 4: A. Suganami et al., Bioorg. Med. Chem. Lett., 2012, 22, 7481-7485

Non-Patent Document 5: S. Ren et al., ACS Appl. Mater. Interfaces., 2017, 9, 31509

Non-Patent Document 6: M. Mitsunaga et al., Nat. Med., 2011, 17, 1685-1691

Non-Patent Document 7: C. Ciliers et al., Cancer Res., 2018, 78, 758

Non-Patent Document 8: K. Fujiwara et al., PLOS ONE, 2015, 10, e0125468

Non-Patent Document 9: K. Berg et al., Cancer Res., 1999, 59, 1180-1183

Non-Patent Document 10: A. A. Sultan et al., Lancet Oncol 2016, 17, 1217-1229

Non-Patent Document 11: Y. Huang et al., J. Porphyrins Phthalocyanines, 2018, 22, 764-770

Non-Patent Document 12: J. Jiang et al., RSC Adv., 2014, 4, 32987-32996

SUMMARY OF INVENTION

Object to be Solved by the Invention

As described above, near infrared light-absorbing dyes that have been currently used as photosensitizers have been problematic, for example, in terms of the insufficient length of the absorption wavelength, the lack of chemical stability, etc. It is an object of the present invention to provide a compound that has absorption in a near infrared region, has high efficiency of singlet oxygen generation (quantum yield), and also has high tumor toxicity when it is combined with an immunotoxin.

Means for Solving the Object

As a result of intensive studies conducted directed towards achieving the aforementioned object, the present inventors have found that, by introducing a novel substituent and a central metal into a phthalocyanine skeleton, the absorption maximum of phthalocyanine can be extended, and also, the singlet oxygen quantum yield can be improved and therapeutic effects can be improved in the photo dynamic therapy. The present invention has been completed based on these findings.

According to the present invention, the following inventions are provided.

<1> A compound represented by the following formula (1) or a salt thereof:

[Formula 1]

-continued (1)

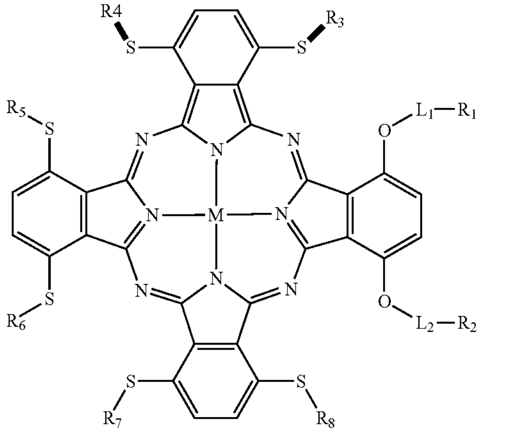

wherein $L_1$ and $L_2$ each independently represent a single bond, —O—, —CO—, an alkylene group containing 1 to 8 carbon atoms, a sugar chain, or a combination thereof; $R_1$ and $R_2$ each independently represent an alkyl group containing 1 to 8 carbon atoms, a carboxylic acid group, an amino group, a hydroxyl group, a thiol group, or a biotin residue; $R_3$, $R_4$, $R_5$, $R_6$, $R_7$ and $R_8$ each independently represent an alkyl group containing 1 to 8 carbon atoms, a phenyl group, a carboxylic acid group, an amino group, a hydroxyl group, a thiol group, or a biotin residue; and M represents Mg, Zn, Fe, P, Si, Cu, Sn, Al, Ti, Mo, or Ni.

<2> The compound according to <1> or a salt thereof, wherein $L_1$ and $L_2$ each independently represent an alkylene group containing 1 to 8 carbon atoms.

<3> The compound according to <1> or <2> or a salt thereof, wherein $R_1$ and $R_2$ each represent a carboxylic acid group.

<4> The compound according to any one of <1> to <3> or a salt thereof, wherein $R_3$, $R_4$, $R_5$, $R_6$, $R_7$, and $R_8$ each represent a phenyl group.

<5> The compound according to any one of <1> to <4> or a salt thereof, wherein M represents Zn.

<6> A medicament for killing tumor cells, comprising the compound according to any one of <1> to <5> or a salt thereof.

<7> The medicament according to <6>, which kills tumor cells according to the following steps:

(1) a step of allowing the compound according to any one of claims 1 to 5 or a salt thereof to come into contact with tumor cells; and (2) a step of killing the tumor cells by irradiating the cells with a wavelength that is effective for activating the compound according to any one of claims 1 to 5 or a salt thereof.

<8> A medicament for killing tumor cells, comprising:

(a) the compound according to any one of <1> to <5> or a salt thereof; and (b) a low-molecular-weight antitumor agent.

<9> The medicament according to <8>, which kills tumor cells according to the following steps:

(1) a step of allowing the compound according to any one of claims 1 to 5 or a salt thereof and the low-molecular-weight antitumor agent to come into contact with tumor cells; and then, (2) a step of killing the tumor cells by irradiating the cells with a wavelength that is effective for activating the compound according to any one of <1> to <5> or a salt thereof.

<10> A medicament for killing tumor cells, comprising:

(a) the compound according to any one of <1> to <5> or a salt thereof; and (b) a conjugate of a substance that binds to a target substance on the surface of tumor cells and a cytotoxin.

<11> The medicament according to <10>, wherein the substance that binds to a target substance on the surface of tumor cells is a conjugate of an antibody or a fragment thereof, a ligand or a peptide, and a cytotoxin.

<12> The medicament according to <9>, wherein the antibody is an antibody reacting against Epidermal Growth Factor Receptor (EGFR, ERBB1, ERBB2, ERBB3, or ERBB4), Mesothelin, Ephrin type-A receptor 2 (EphA2), Glypican3 (GPC3), Cadherin17 (CDH17), Cadherin3 (CDH3), or Roundabout homolog 1 (Robo1).

<13> The medicament according to any one of <8> to <10>, wherein the cytotoxin is saporin, gelonin, or *Pseudomonas* exotoxin.

<14> The medicament according to any one of <10> to <13>, which kills tumor cells according to the following steps:

(1) a step of allowing the compound according to any one of <1> to <5> or a salt thereof and the conjugate to come into contact with tumor cells; and then, (2) a step of killing the tumor cells by irradiating the cells with a wavelength that is effective for activating the compound according to any one of <1> to <5> or a salt thereof.

<15> The medicament according to any one of <1> to <14>, wherein the tumor cells are cancer cells of any one of head and neck cancer, lung cancer, liver cancer, colorectal cancer, skin cancer, esophageal cancer, stomach cancer, cervical cancer, endometrial cancer, mesothelioma, brain tumor, malignant melanoma, breast cancer, bile duct cancer, pancreatic cancer, ovarian cancer, kidney cancer, bladder cancer, prostate cancer, malignant lymphoma, and osteosarcoma.

Advantageous Effects of Invention

The compound of the present invention has absorption in a near infrared region, has high efficiency of singlet oxygen generation (quantum yield), and also has high tumor toxicity when it is combined with an immunotoxin.

BRIEF DESCRIPTION OF DRAWINGS

FIG. 1 shows the absorption spectrum of PS1 in DMSO.

FIG. 2 shows a plot of absorption vs. concentration.

FIG. 3 shows the absorption spectrum of PS1 and DPBF in DMSO after irradiation (for 0 to 60 seconds) with a light (λ=775 nm).

FIG. 4 shows the cell viability of A431 cells after a treatment with PS1 and NIR.

FIG. 5 shows the absorption spectrum of PS1 remaining in A431 cells at 0 to 24 hours after the removal of the PS1.

FIG. 6 shows a plot of the amount of PS1 after the removal of the PS1 and the incubation time.

FIG. 7 shows the results of ELISA with panitumumab-biotin (primary antibody: streptavidin-poly HRP).

FIG. 8 shows the cell viability of A431 cells treated with immunotoxin (IT) and photochemical internalization (PCI).

FIG. 9 shows the viability of A431 cells treated with IT and PCI (PS1+NIR).

FIG. 10 shows the cell viability of A431 cells treated with non-target IT (B8109B-saporin) and PCI (PS1+NIR).

FIG. 11 shows the absorption maximum and singlet oxygen quantum yield of PS1 and common photosensitizers. The absorption maximum of all of the substances was measured in DMSO. The singlet oxygen quantum yield was measured in DMSO (PS1 and ZnPc) or in a buffer aqueous solution (pH 7.4) (AlPcS2α and ICG).

FIG. 12 shows the cell viability of A431 cells treated with IT and PCI (photosensitizer+NIR).

FIG. 13 shows the confocal microscope imaging (before irradiation with NIR 18) of A431 cells treated with an FITC antibody and PS1. From the left, a fluorescein-labeled antibody (λex=488 nm, pinhole: 800 μm, master gain: 800, digital offset: 0, digital gain: 1.00), Hoechst33342 (λex=405 nm, pinhole: 800 μm, master gain: 633, digital offset: 0, digital gain: 1.00), image overlapping (fluorescein and Hoechst33342), and image overlapping (fluorescein, Hoechst33342 and DIC) are shown.

FIG. 14 shows the confocal microscope imaging of A431 cells treated with an FITC antibody and PS1 (after irradiation with NIR). From the left, a fluorescein-labeled antibody (λex=488 nm, pinhole: 800 μm, master gain: 800, digital offset: 0, digital gain: 1.00), Hoechst33342 (λex=405 nm, pinhole: 800 μm, master gain: 633, digital offset: 0, digital gain: 1.00), image overlapping (fluorescein and Hoechst33342), and image overlapping (fluorescein, Hoechst33342 and DIC) are shown.

FIG. 15 shows quantification of FITC fluorescence intensity/cells.

FIG. 16 shows the cell viability of A549 cells treated with PS1 and NIR irradiation.

FIG. 17 shows the cell viability of A549 cells treated with IT and PCI (PS1+NIR).

FIG. 18 shows the cell viability of HEK293T cells treated with PS1 and NIR irradiation.

FIG. 19 shows the cell viability of HEK293T cells treated with IT and PCI (PS1+NIR).

FIG. 20 shows hemolysis percentage obtained by PS1 (Zn6PTPc).

FIG. 21 shows the flow cytometric analysis of an annexin PI staining assay.

FIG. 21(*a*) shows size distribution; FIG. 21(*b*) shows a legend of FIG. 21(*c*); FIG. 21(*c*) shows fluorescence distribution in the cells in R1 in FIG. 21(*a*). X axis shows annexin fluorescence and Y axis shows PI.

FIG. 22 shows the results of an experiment using cancer-bearing mice.

EMBODIMENTS OF CARRYING OUT THE INVENTION

Hereinafter, the embodiments of carrying out the present invention will be described in detail.

<Compound of the Present Invention>

The present invention relates to a compound represented by the following formula (1) or a salt thereof:

[Formula 2]

(1)

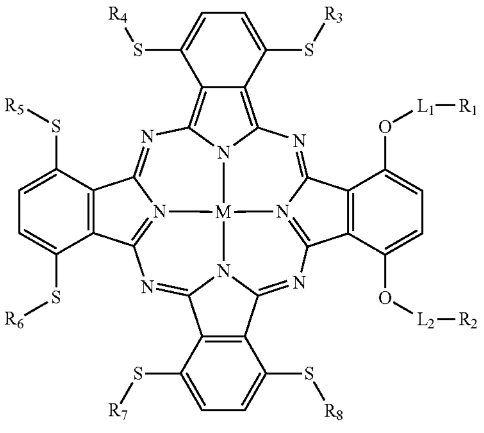

wherein individual substituents are as defined later.

The compound of the present invention has, at the position a thereof, a thio group that is an electron-donating group for destabilizing the energy level of HOMO and extending the absorption wavelength. Since the position a of phthalocyanine has a larger molecular orbital coefficient than the position p thereof, the energy level of HOMO is destabilized by introducing such an electron-donating group into the position a, so that the absorption wavelength of the phthalocyanine can be shifted to the long wavelength side.

The compound of the present invention or a salt thereof is a sensitizer that is activated with a light and induces photochemical internalization. The compound of the present invention or a salt thereof can generate singlet oxygen by being activated with a light.

$L_1$ and $L_2$ each independently represent a single bond, —O—, —CO—, an alkylene group containing 1 to 8 carbon atoms, a sugar chain, or a combination thereof. $L_1$ and $L_2$ may be, for example, —OCO— or —COO—, in which —O— is combined with —CO—, or may also be a group formed by combining any one or more of —O—, —CO—, —OCO— or —COO—, with one or more alkylene groups containing 1 to 8 carbon atoms. $L_1$ and $L_2$ each represent preferably an alkylene group containing 1 to 8 carbon atoms, more preferably an alkylene group containing 1 to 6 carbon atoms, and further preferably an alkylene group containing 1 to 4 carbon atoms.

$R_1$ and $R_2$ each independently represent an alkyl group containing 1 to 8 carbon atoms, a carboxylic acid group, an amino group, a hydroxyl group, a thiol group, or a biotin residue. $R_1$ and $R_2$ are preferably carboxylic acid groups.

$R_3$, $R_4$, $R_5$, $R_6$, $R_7$ and $R_8$ each independently represent an alkyl group containing 1 to 8 carbon atoms, a phenyl group, a carboxylic acid group, an amino group, a hydroxyl group, a thiol group, or a biotin residue. $R_3$, $R_4$, $R_5$, $R_6$, $R_7$ and $R_8$ each independently, namely, may be the same as or different from one another. Preferably, $R_3$, $R_4$, $R_5$, $R_6$, $R_7$ and $R_8$ are the same groups as one another.

$R_3$, $R_4$, $R_5$, $R_6$, $R_7$ and $R_8$ are preferably phenyl groups.

M represents Mg, Zn, Fe, P, Si, Cu, Sn, Al, Ti, Mo or Ni. M particularly preferably represents Zn.

The method of synthesizing the compound of the present invention is not particularly limited, and the present compound can be synthesized according to the method described in the after-mentioned Examples. Depending on the types of substituents in the formula (1), by using reagents corresponding to the substituents, the compound of the formula (1) can be synthesized.

<Medicament for Killing Tumor Cells>

The medicament of the present invention includes the following three embodiments.

A first embodiment is a medicament for killing tumor cells, comprising the compound represented by the formula (1) or a salt thereof.

In this embodiment, tumor cells can be killed by (1) a step of allowing the compound represented by the formula (1) or a salt thereof to come into contact with tumor cells; and (2) a step of killing the tumor cells by irradiating the cells with a wavelength that is effective for activating the compound represented by the formula (1) or a salt thereof.

A second embodiment is a medicament for killing tumor cells, comprising (a) the compound represented by the formula (1) or a salt thereof, and (b) a low-molecular-weight antitumor agent.

In this embodiment, tumor cells can be killed by (1) a step of allowing the compound represented by the formula (1) or a salt thereof and the low-molecular-weight antitumor agent to come into contact with tumor cells; and then, (2) a step of killing the tumor cells by irradiating the cells with a wavelength that is effective for activating the compound represented by the formula (1) or a salt thereof.

In the present invention, a low-molecular-weight antitumor agent binds to a tumor, and it is then enclosed in the endosome. A light is applied to the compound represented by the formula (1) (i.e. a photosensitizing dye), which has been added separately (or simultaneously), so that the low-molecular-weight antitumor agent enclosed in the endosome is allowed to release into the cytoplasm, and the tumor cells can be thereby killed.

The order of allowing the compound represented by the formula (1) or a salt thereof and the low-molecular-weight antitumor agent to come into contact with tumor cells is not particularly limited. After the compound represented by the formula (1) or a salt thereof has been administered to tumor cells, the low-molecular-weight antitumor agent may be administered thereto. Otherwise, after the low-molecular-weight antitumor agent has been administered to tumor cells, the compound represented by the formula (1) or a salt thereof may be administered thereto. Alternatively, the compound represented by the formula (1) or a salt thereof and the low-molecular-weight antitumor agent may be simultaneously administered to tumor cells.

A third embodiment is a medicament for killing tumor cells, comprising (a) the compound represented by the formula (1) or a salt thereof, and (b) a conjugate of a substance that binds to a target substance on the surface of tumor cells and a cytotoxin.

In this embodiment, tumor cells can be killed by (1) a step of allowing the compound represented by the formula (1) or a salt thereof and the conjugate to come into contact with tumor cells; and then, (2) a step of killing the tumor cells by irradiating the cells with a wavelength that is effective for activating the compound represented by the formula (1) or a salt thereof.

In the present invention, the conjugate of a substance that binds to a target substance on the surface of tumor cells and a cytotoxin binds to a tumor, and it is then enclosed in the endosome. A light is applied to the compound represented by the formula (1) (i.e. a photosensitizing dye), which has been added separately (or simultaneously), so that the conjugate (i.e. an immunotoxin) (or a decomposed product thereof) enclosed in the endosome is allowed to release into the cytoplasm, and the tumor cells can be thereby killed.

The order of allowing the compound represented by the formula (1) or a salt thereof and the conjugate of a substance that binds to a target substance on the surface of tumor cells and a cytotoxin to come into contact with tumor cells is not particularly limited. After the compound represented by the formula (1) or a salt thereof has been administered to tumor cells, the conjugate may be administered thereto. Otherwise, after the conjugate has been administered to tumor cells, the compound represented by the formula (1) or a salt thereof may be administered thereto. Alternatively, the compound represented by the formula (1) or a salt thereof and the conjugate may be simultaneously administered to tumor cells.

<Low-Molecular-Weight Antitumor Agent>

A preferred example of the anticancer agent used in the present invention is bleomycin. Other preferred examples of the anticancer agent used in the present invention may include anticancer antibiotics, alkylating agents, platinum compounds, antimetabolites, topoisomerase inhibitors, anticancer antibiotics, microtubule-acting anticancer agents (alkaloid anticancer agents), molecular target drugs (kinase inhibitors, etc.), immunomodulators, DNA intercalators or DNA crosslinkers, DNA synthesis inhibitors, and DNA and/or RNA transcription inhibitors.

<Substance that Binds to Target Substance on Surface of Tumor Cells>

Examples of the substance that binds to a target substance on the surface of tumor cells may include an antibody or a fragment thereof, a ligand, and a peptide, but the examples are not limited thereto.

When an antibody is used as such a substance that binds to a target substance on the surface of tumor cells, there can be used an antibody specifically binding to a target substance on the surface of tumor cells (e.g. a protein such as Epidermal Growth Factor Receptor (EGFR, ERBB1, ERBB2, ERBB3, or ERBB4), Mesothelin, Ephrin type-A receptor 2 (EphA2), Glypican3 (GPC3), Cadhelin17 (CDH17), Cadherin3 (CDH3), Roundabout homolog 1 (Robo1), or CD20).

The type of the antibody is not particularly limited, and examples of the present antibody may include a mouse antibody, a human antibody, a rat antibody, a rabbit antibody, a sheep antibody, a camel antibody, an avian antibody, and a genetically modified antibody that is artificially modified for the purpose of reducing xenoantigenicity against a human, such as a chimeric antibody or a humanized antibody. Such a genetically modified antibody can be produced by applying a known method. The chimeric antibody is an antibody consisting of the heavy chain and light chain variable regions of a mammalian antibody other than a human antibody, such as a mouse antibody, and the heavy chain and light chain constant regions of a human antibody. The chimeric antibody can be obtained by ligating DNA encoding the variable region of a mouse antibody to DNA encoding the constant region of a human antibody, then incorporating the ligate into an expression vector, and then introducing the expression vector into a host, so that the host is allowed to generate the antibody. The humanized antibody is obtained by transplanting the complementarity determining region (CDR) of a mammalian antibody other than a human antibody, such as a mouse antibody, into the complementarity determining region of a human antibody. A common gene recombination method therefor has been known. Specifically, a DNA sequence designed to ligate the CDR of a mouse antibody to the framework region (FR) of a human antibody is synthesized from several oligonucleotides that have been produced such that they have an overlapping portion at the terminal portions thereof according to a PCR method. The obtained DNA is ligated to DNA encoding the constant region of a human antibody, and the ligate is then incorporated into an expression vector, which is then introduced into a host, so that the host is allowed to generate the antibody (EP 239400, International Publication WO96/02576, etc.).

In addition, a method of obtaining a human antibody has also been known. For example, human lymphocytes are sensitized with a desired antigen or a cell expressing the desired antigen in vitro, and then fusing the sensitized lymphocytes with human myeloma cells, such as, for example, U266, so as to obtain a desired human antibody having a binding activity to an antigen (JP Paten Publication (Kokoku) No. 1-59878 B (1989)). Otherwise, a transgenic antibody having all repertoires of human antibody genes is immunized with a desired antigen to obtain a desired human antibody (see WO93/12227, WO92/03918, WO94/02602, WO94/25585, WO96/34096, and WO96/33735). Further, a technique of obtaining a human antibody by panning using a human antibody library has also been known. For example, a human antibody variable region is allowed to express as a single chain antibody (scFv) on the surface of a phage according to a phage display method, and a phage binding to an antigen can be then selected. By analyzing the selected phage gene, a DNA sequence encoding the variable region of a human antibody binding to the antigen can be determined. If the DNA sequence of scFv binding to an antigen is clarified, a suitable expression vector comprising the sequence can be produced, so that a human antibody can be obtained. These methods have already been publicly known, and please refer to WO92/01047, WO92/20791, WO93/06213, WO93/11236, WO93/19172, WO95/01438, and WO95/15388.

The antibody that binds to tumor cells is preferably a humanized or a human antibody, but is not limited thereto.

Moreover, these antibodies may also be low molecular weight antibodies such as antibody fragments, or modified forms of the antibodies, unless they lose the property of recognizing the entire or a part of a protein encoded by an antigen gene present on the surface of tumor cells. The antibody fragment is a part of an antibody that retains a binding ability to ROBO1. Specific examples of the antibody fragment may include Fab, Fab', F(ab')2, Fv, Diabody, and a single chain variable fragment (scFv). In order to obtain such an antibody fragment, a gene encoding such an antibody fragment is constructed, the gene is then introduced into an expression vector, and it may be then expressed in suitable host cells. As a modified form of an antibody, an antibody binding to various types of molecules such as polyethylene glycol (PEG) can also be used.

DNA encoding a monoclonal antibody can be easily isolated and sequenced according to a commonly used method (for example, by using an oligonucleotide probe capable of specifically binding to a gene encoding the heavy chain and light chain of the monoclonal antibody). Hybridoma cells may be preferable starting materials for such DNA. Once such DNA is isolated, it is inserted into an expression vector, and the expression vector is then used to transform host cells such as *E. coli* cells, COS cells, CHO cells, or myeloma cells that do not generate immunoglobulin before they are transformed. Then, a monoclonal antibody can be generated from the transformed host cells.

As a substance that binds to a target substance on the surface of tumor cells, a ligand can be used. When the target substance on the surface of tumor cells is, for example, a receptor such as Epidermal Growth Factor Receptor (EGFR, ERBB1, ERBB2, ERBB3, or ERBB4), Mesothelin, or Ephrin type-A receptor 2 (EphA2), a ligand against each of the above-described receptors can be used.

The target of the antibody is set to be an epidermal growth factor receptor (EGFR). EGFR is a receptor that recognizes an epidermal growth factor associated with the proliferation or growth of cells and carries out signal transduction. Even in the case of normal cells, 40,000 to 100,000 molecules of EGFR are expressed in a single normal cell [15]. In many cancers such as breast cancer, bladder cancer, colon cancer, glioma, non-small cell lung cancer, pancreatic cancer, ovarian cancer, and head and neck cancer, the expression of 1,000,000 molecules or more of EGFR has been confirmed in a single cancer cell [16]. Moreover, it has bene reported that a tumor involving the overexpression of EGFR exhibits higher proliferative ability and higher metastatic ability than a tumor that does not involve the overexpression of EGFR, and that such a tumor involving the overexpression of EGFR shows resistance to conventional chemotherapy and radiation therapy [17]. Accordingly, EGFR has already become a common target of cancer therapy. An EGFR tyrosine kinase inhibitor, gefitinib (IRESSA), binds to the ATP-binding site of the tyrosine kinase of EGFR, while competing against ATP, so that this drug inhibits the autophosphorylation of EGFR and blocks signal transduction [18]. Gefitinib has been approved in 2002 also in Japan, and has been used in the treatment of non-small cell lung cancer. In addition, antibody drugs targeting EGFR, namely, cetuximab and panitumumab have also been approved in Japan in 2008 and in 2010, respectively, and these drugs have been used in clinical treatments. Thus, EGFR used as a target of molecular target drugs in clinical sites was selected as a common antibody target.

As such a substance that binds to a target substance on the surface of tumor cells, a peptide can also be used. A peptide that binds to a target substance on the surface of tumor cells can be designed and produced by those skilled in the art.

<Cytotoxin>

The cytotoxin is preferably a protein having cytotoxicity, but is not limited thereto. The cytotoxin may also be a compound having a synthetic or natural anticancer action, such as bleomycin, or a compound used in ADC.

Preferred examples of such a protein having cytotoxicity may include saporin, gelonin, *Pseudomonas* Endotoxin, ricin A chain, deglycosylated ricin A chain, a ribosome inactivating protein, alphasarcine, aspergillin, restrictocin, ribonuclease, epipodophyllotoxin, diphtheria toxin, Shiga-toxin, and a mutant or a genetically modified body thereof.

Moreover, an anticancer agent that hardly transfers from the endosome into the cytoplasm can also be used.

A preferred example of the cytotoxin is saporin. Saporin is a proteinaceous toxin contained in the seeds of *Saponaria officinalis*, and saporin inactivates the ribosome and thereby causes cell death. Saporin alone is incorporated into a cell only by a passive method such as pinocytosis, and thus, its cellular uptake efficiency is low. Therefore, it has been known that saporin can be incorporated into a cell only after it is allowed to bind to an antibody to form an immunotoxin, and then that saporin can finally exhibit toxicity.

<Conjugate of Substance that Binds to Target Substance on Surface of Tumor Cells and Cytotoxin>

A substance that binds to a target substance on the surface of tumor cells, and a cytotoxin, must bind to each other, directly or indirectly.

When an antibody or a fragment thereof is used as such a substance that binds to a target substance on the surface of tumor cells, as a method of directly chemically binding the antibody or the fragment thereof to a cytotoxin, a binding method used for known ADC (Antibody Drug Conjugate)

can be used. Otherwise, when the cytotoxin is a protein, a bifunctional crosslinking agent can also be used.

Alternatively, when the cytotoxin is a protein, a toxin is fused with an antibody or a fragment thereof by genetic recombination to form a protein, so that an immunotoxin can be produced.

Moreover, as another method, a method of indirectly binding an antibody or a fragment thereof to a cytotoxin by using a second binding pair can also be used. Examples of the second binding pair that can be utilized herein may include avidin-biotin and an antibody-hapten.

Further, in the present invention, it is also possible to use a conjugate of a peptide or a ligand that binds to a target substance on the surface of tumor cells and a toxin, instead of using an immunotoxin in which an antibody and a toxin bind to each other.

<Administration Methods and Applied Doses>

The method for administering the medicament of the present invention to a subject having a tumor (for example, a cancer, etc.) is not particularly limited.

The compound represented by the formula (1) of the present invention or a salt thereof can be administered to a subject, for example, via intravenous administration, arterial administration, intramuscular administration, subcutaneous administration, intradermal administration, intraperitoneal administration, or oral administration. Alternatively, there may also be an administration method involving administration of the compound represented by the formula (1) or a salt thereof to tumor tissues and the periphery thereof via local injection, application, spraying, etc.

The low-molecular-weight antitumor agent can be administered to a subject, for example, via intravenous administration, arterial administration, intramuscular administration, subcutaneous administration, intradermal administration, intraperitoneal administration, or oral administration. Alternatively, there may also be an administration method involving administration of the compound represented by the formula (1) or a salt thereof to tumor tissues and the periphery thereof via local injection, application, spraying, etc.

The conjugate of a substance that binds to a target substance on the surface of tumor cells and a cytotoxin can be administered to a subject, for example, via intravenous administration, arterial administration, intramuscular administration, subcutaneous administration, intradermal administration, intraperitoneal administration, or oral administration. Alternatively, there may also be an administration method involving administration of the compound represented by the formula (1) or a salt thereof to tumor tissues and the periphery thereof via local injection, application, spraying, etc.

The applied dose of the compound represented by the formula (1) of the present invention or a salt thereof is not particularly limited. The compound represented by the formula (1) of the present invention or a salt thereof can be administered to a subject at a dose of, for example, 1 μg/kg of body weight to 100 mg/kg of body weight, and preferably, at a dose of 10 μg/kg of body weight to 10 mg/kg of body weight.

The applied dose of the low-molecular-weight antitumor agent is not particularly limited, and it can be administered to a subject at a dose of, for example, 1 μg/kg of body weight to 100 mg/kg of body weight, and preferably, at a dose of 10 μg/kg of body weight to 10 mg/kg of body weight.

The applied dose of the conjugate of a substance that binds to a target substance on the surface of tumor cells and a cytotoxin is not particularly limited, and it can be administered to a subject at a dose of, for example, 1 μg/kg of body weight to 100 mg/kg of body weight, and preferably, at a dose of 10 μg/kg of body weight to 10 mg/kg of body weight.

The number of administration is not particularly limited, and administration can be carried out once to several times (from once to 20 times, and preferably from once to 10 times). Administration can be carried out, for example, every 2 to 4 weeks, or every 1 to 2 months. In addition, the number of light irradiation operations is not particularly limited, either. The light irradiation can be carried out once to several times.

<Tumors as Targets>

The tumor as a target of the administration of the medicament of the present invention is not particularly limited. Examples of the tumor may include cancers, such as head and neck cancer, lung cancer, liver cancer, colorectal cancer, skin cancer, esophageal cancer, stomach cancer, cervical cancer, endometrial cancer, mesothelioma, brain tumor, malignant melanoma, breast cancer, bile duct cancer, pancreatic cancer, ovarian cancer, kidney cancer, bladder cancer, prostate cancer, malignant lymphoma, and osteosarcoma.

The tumor cells are preferably tumors that express, on the surface thereof, Epidermal Growth Factor Receptor (EGFR, ERBB1, ERBB2, ERBB3, or ERBB4), Mesothelin, Ephrin type-A receptor 2 (EphA2), Glypican3 (GPC3), Cadhelin17 (CDH17), Cadhelin3 (CDH3), Roundabout homolog 1 (Robo1), CD20, etc.

The present invention will be specifically described in the following examples. However, these examples are not intended to limit the scope of the present invention.

EXAMPLES

<Synthesis of Phthalonitrile Pn3>

[Formula 3]

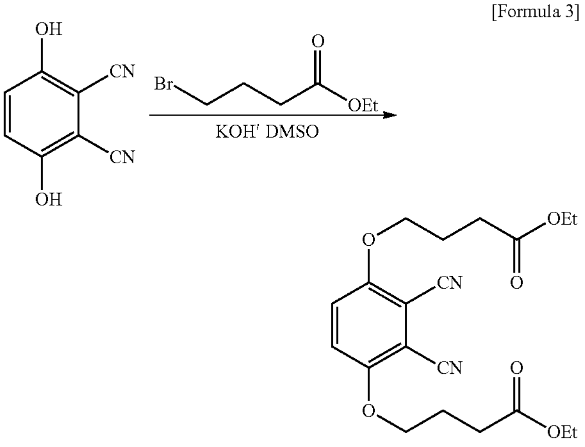

2,3-Dicyanohydroquinone (1.0 g, 6.24 mmol), ethyl 4-bromobutyrate (3.57 mL, 24.5 mmol), and potassium hydroxide were dissolved in dimethyl sulfoxide (30 mL), and the obtained solution was then stirred at room temperature for 18 hours. Thereafter, water was added to the reaction mixture, and a generated precipitate was then recovered. The recovered precipitate was washed with water, and was then dried under reduced pressure to obtain a product of interest (2.12 g, 88%). Since the obtained product was a known compound, NMR assignment was carried out according to the publication (T. Goslinski et al., Polyhedron, 2011, 30, 1538-1546).

1H NMR (DMSO d6) d 7.62 (s, 2H), 4.18 (t, J=6.0, 4H), 4.07 (q, J=7.1, 4H), 2.38 (t, 2H), 1.98 (qui, J=6.9, 4H), 1.78 (t, J=6.9, 6H);

ESI-MS (positive, smart) [M+Na]+411.1527 (found), 411.1527 (calcd).

<Synthesis of Phthalonitrile Pn4>

[Formula 4]

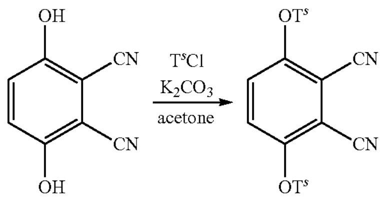

Since this compound was a known compound, the reaction was carried out according to the publication (N. Kobayashi et al., J. Am. Chem. Soc., 2011, 133, 19642-19645). 2,3-Dicyanohydroquinone (1.0 g, 6.0 mmol) and p-toluenesulfonyl chloride (2.6 g, 14 mol) were dissolved in acetone (8 mL), and potassium carbonate (3.5 g, 25 mmol) was then added to the solution, followed by refluxing for 2 hours. Thereafter, the reaction mixture was cooled to room temperature, and cold water was then added to the mixture. A generated precipitate was recovered, and the recovered precipitate was then washed with water to obtain a product of interest. The yield was 2.86 g, and the yield percentage was 98%.

1H NMR (DMSO d6) d 7.81 (d, J=4.1, 4H), 7.75 (s, 2H), 7.56 (d, J=4.1, 4H), 2.47 (s, 6H);

ESI-MS (pos.smart) [M+Na]+491.0346 (found), 491.0342 (calcd).

<Synthesis of Phthalonitrile Pn5>

[Formula 5]

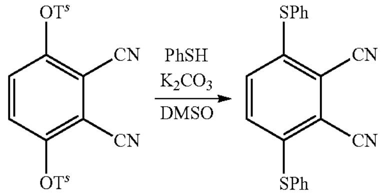

Since this compound was a known compound, the reaction was carried out according to the publication (N. Kobayashi et al., J. Am. Chem. Soc., 2011, 133, 19642-19645). Phthalonitrile Pn4 (1.0 g, 2.13 mmol), thiophenol (0.9 mL, 8.54 mmol), and potassium carbonate (1.18 g, 8.54 mmol) were added to dimethyl sulfoxide (25 mL), and the obtained solution was then stirred at room temperature for 18 hours. Thereafter, water was added to the reaction mixture, and the reaction solution was then extracted with chloroform to recover an organic layer. The recovered organic layer was washed with a sodium hydrogen carbonate aqueous solution, and was then dried over magnesium sulfate. Thereafter, the solvent was removed under reduced pressure to obtain a crude product. The crude product was purified by silica gel column chromatography (chloroform: hexane=3:1), and was then recrystallized with methanol to obtain a product of interest (411 mg, 56%).

1H NMR (CDCl3) d 7.41-7.49 (in, 10H), 6.95 (s, 2H);

ESI-MS (pos. smart) [M+Na]+367.0334 (found), 367.0334 (calcd).

<Synthesis of Phthalocyanine H2Pc6>

[Formula 6]

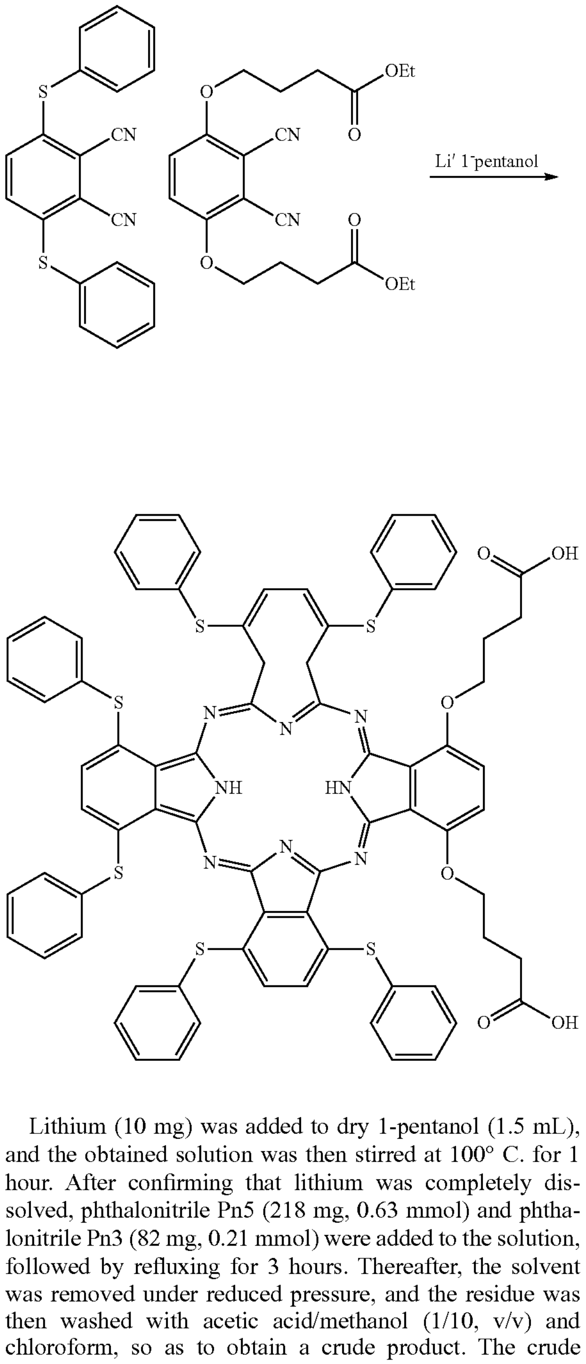

Lithium (10 mg) was added to dry 1-pentanol (1.5 mL), and the obtained solution was then stirred at 100° C. for 1 hour. After confirming that lithium was completely dissolved, phthalonitrile Pn5 (218 mg, 0.63 mmol) and phthalonitrile Pn3 (82 mg, 0.21 mmol) were added to the solution, followed by refluxing for 3 hours. Thereafter, the solvent was removed under reduced pressure, and the residue was then washed with acetic acid/methanol (1/10, v/v) and chloroform, so as to obtain a crude product. The crude product was purified by silica gel column chromatography (chloroform:methanol=15:1; 1% acetic acid) to obtain a product of interest (29.7 mg, 10%).

MALDI-TOF-MS (LP 0-2 kDa) [M+H]+ 1368.453 (found), 1368.689 (calcd).

<Synthesis of Zinc Phthalocyanine PS1>

[Formula 7]

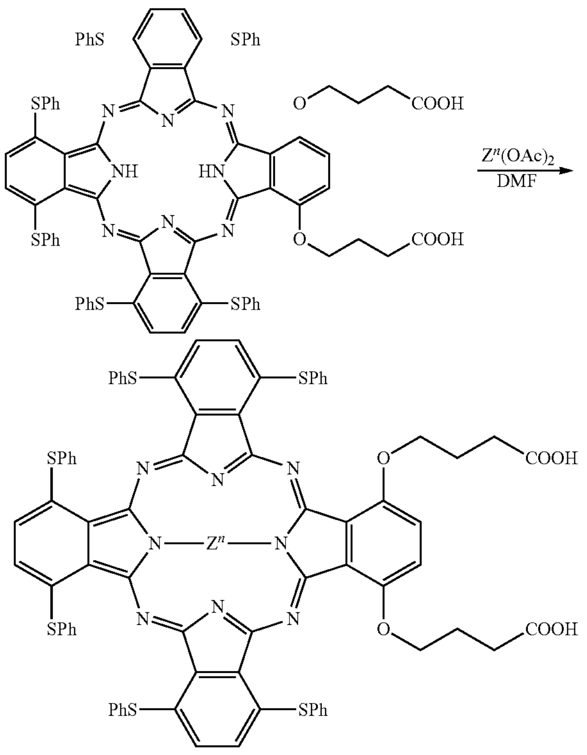

Phthalocyanine H2Pc6 (29.7 mg, 22 μmol) and zinc acetate (23.9 mg, 0.109 mmol) were dissolved in N,N-dimethylformamide (2 mL), and the obtained solution was then stirred at 100° C. for 5 hours. Thereafter, the solvent was removed under reduced pressure, and the product was then purified by column chromatography (chloroform: methanol=15:1; 1% acetic acid) to obtain a product of interest (20.8 mg, 85%).

H NMR (DMSO d6) d 7.91 (d, J=6.6, 4H), 7.75 (m, 12H), 7.65 (m, 6H), 7.51 (m, 12H), 7.20 (d, J=7.4, 2H), 7.06 (d, J=9.2, 2H),

MALDI-TOF-MS (LP_0-2 kDa) [M+H]+ 1432.309 (found), 1432.054 (calcd).

<Measurement of Optical Properties of ZnPc6>

The absorption spectrum of the synthesized PS1 was measured. The absorption spectrum of the PS1 in dimethyl sulfoxide was as shown in FIG. 1, and the maximum absorption wavelength in the Q band was 775 nm. In addition, absorption spectra were measured at different concentrations, and the absorption at a wavelength of 775 nm was then plotted to obtain a molar adsorption coefficient. As a result, the molar adsorption coefficient was 41000 ($M^{-1}$ $cm^{-1}$) (FIG. 2).

<Measurement of Singlet Oxygen Quantum Yield of PS1>

The singlet oxygen quantum yield of PS1 was measured. PS1 and DPBF were dissolved in dimethyl sulfoxide, and the absorption spectrum was then measured every time when a light with a wavelength of 775 nm was applied to the obtained solution for 5 seconds. The results was as shown in FIG. 3. From these results, it could be confirmed that the absorption at a wavelength of 416 nm was reduced as the light irradiation time became long, and that DPBF reacted with singlet oxygen. As a result of calculation of the singlet oxygen quantum yield, it was found to be 0.61. This value was higher than the values of conventional photosensitizers, and thus, the usefulness of PS1 for photo dynamic therapy could be expected.

<Cytotoxicity Caused by PS1 and Near Infrared Light Irradiation>

In order to confirm the ability of PS1 to release singlet oxygen in cells, a cell experiment was carried out. First, A431 cells (10,000 cells/well) were seeded on a 96-well plate, and 24 hours later, PS1 (0 to 20 μM) was added thereto. Eighteen hours later, the medium containing PS1 was removed, and the cells were then washed with PBS. After that, a new medium was added, and irradiation (6.1 $mW/cm^2$ for 60 min, 22 $J/cm^2$) with a near infrared light (700 to 1100 nm) was then carried out. Forty-eight hours after the irradiation, CCK-8 was added to the resultant, and the absorption at a wavelength of 450 nm was then measured using a plate reader, so that cell viability was measured (FIG. 4). A reduction in the cell viability was not found regardless of the presence or absence of near infrared light irradiation, when the concentration of PS1 was 4 μM or less. However, when PS1 was used in a concentration of 20 μM, the cell viability was significantly reduced only under the near infrared light irradiation. From these results, it was confirmed that PS1 can release singlet oxygen in a cellular environment as a result of near infrared light irradiation.

<Evaluation of Retentivity of PS1 in Cells>

Retentivity of PS1 in cells was evaluated. When PS1 remains in the body of a patient administered with the PS1, without being discharged from the cells, the patient must stay in a dark room until the PS1 is completely discharged from the body, in order to avoid the damage caused by singlet oxygen given to organs such as skin in undesired sites as a result of the photosensitizative action. Thus, prompt discharge from the inside of a body is one of properties that should be possessed by photosensitizers. In order to evaluate the retentivity of PS1 in cells, the following experiment was carried out (S. Hirohara et al., J. Photochem. Photobiol., B, 2005, 78, 7-15).

A431 cells (50,000 cells/well) were seeded on a 24-well plate, and 24 hours later, PS1 (10 μM) was added thereto. Eighteen hours later, the medium containing PS1 was removed, and the cells were then washed with PBS. After that, a new medium was added, and incubation was further continued (0, 1, 2, 4, and 24 hours). Thereafter, the cells were washed with PBS again, and DMSO (150 μL) was added to the resultant cells, followed by shaking for 1 hour. Thereafter, the absorption spectrum of the obtained DMSO solution was measured, and PS1 remaining in the cells was then quantified (FIG. 5). As a result, it was found that 52% of PS1 was released to the outside of the cells, after PS1 had been removed and incubation had been carried out for 24 hours (FIG. 6). Since real cells are present in a more fluctuating environment, the discharge of PS1 is considered to be faster than the case of culturing the cells on a culture dish.

<Biotinylation of Anti-EGFR Antibody Panitumumab>

In order to produce an immunotoxin that targets EGFR, biotinylation of an anti-EGFR antibody, panitumumab, was carried out. As a method of biotinylating panitumumab, a higher efficient NHS ester method was adopted. Sulfo-NHS-biotin (10 mM, 1.33 μL) was added to panitumumab (1 mg/mL, 50 μL) in an amount of 40 equivalents relative to the amount of panitumumab, and the obtained mixture was then reacted at room temperature for 1 hour. Thereafter, the reaction solution was purified by spin column chromatography to obtain a biotinylated antibody. Progression of the biotinylation of the antibody was confirmed by ELISA. Panitumumab-biotin or panitumumab was immobilized on a 96-well plate, and thereafter, streptavidin-poly HRP was allowed to react as a primary antibody with the panitumumab-biotin or the panitumumab. After that, detection was carried out according to an enzymatic reaction of tetramethylbenzidine. The results obtained after addition of the streptavidin-poly HRP was as shown in FIG. 7, and only the panitumumab-biotin was reacted. Thus, it was confirmed that biotinylation of panitumumab progressed. This biotinylated antibody was mixed with 1 equivalent of streptavidin-saporin, so as to obtain an immunotoxin (panitumumab-saporin).

<Cell Experiment Using EGFR-Overexpressing A431 Cells>

A cell experiment was carried out using A431 cells that had been confirmed to express EGFR at a significantly high level. As described regarding cytotoxicity caused by PS1 and near infrared light irradiation, it was confirmed that PS1 exhibits cytotoxicity only under the near infrared light irradiation, when the PS1 is used in a concentration of 20 μM. Accordingly, in photochemical internalization (PCI), the concentration of PS1 was set to be 1 μM and 5 μM, in which cytotoxicity was not exhibit only by PS1 and near infrared light irradiation. First, A431 cells (10,000 cells/well) were seeded on a 96-well plate, and 24 hours later, an immunotoxin (panitumumab-saporin, 0 to 4 nM) and PS1 (1 μM or 5 μM) were added thereto. Eighteen hours later, the medium containing the immunotoxin and PS1 was removed, and the cells were then washed with PBS. After that, a new medium was added, and irradiation (6.1 $mW/cm^2$ for 60 min, 22 $J/cm^2$) with a near infrared light (700 to 1100 nm) was then carried out. Forty-eight hours after the irradiation, CCK-8 was added to the resultant, and the absorption at a wavelength of 450 nm was then measured using a plate reader, so that cell viability was measured (FIG. 8). As a result, a reduction in the cell viability was not found by the single use of 160 pM or less of the immunotoxin. On the other hand, when PCI was used in combination with the immunotoxin, the cell viability was significantly reduced even with 6.4 pM of the immunotoxin. Moreover, when only PCI was carried out without addition of the immunotoxin (0 pM of IT in FIG. 8), a significant reduction in the cell viability was not observed. From these results, it was found that the cytotoxic ability of the immunotoxin is significantly enhanced by PCI using PS1.

Next, a cell experiment was carried out, while changing conditions regarding the presence or absence of addition of PS1 and the presence or absence of near infrared light irradiation. The results was as shown in FIG. 9. A significant reduction in the cell viability was observed only in the cells, on which both addition of PS1 and near infrared light irradiation were carried out, as well as addition of the immunotoxin. From these results, it was suggested that singlet oxygen generated by addition of PS1 and the near infrared light irradiation would be likely to contribute to the improvement of the cytotoxic ability of the immunotoxin.

Subsequently, the same experiment as described above was carried out using a non-specific immunotoxin produced from B8109B-biotin. The results was as shown in FIG. 10. When such a non-specific immunotoxin was used, a significant reduction in the cell viability was not observed even if both addition of PS1 and near infrared light irradiation were carried out. From these results, it was found that the immunotoxin was first incorporated into cells having specific antigens, and that the cytotoxic ability of the immunotoxin was then enhanced according to PCI.

Subsequently, the photosensitization ability of PS1 under near infrared light irradiation was compared with those of conventional photosensitizers. As such conventional photosensitizers, AlPcS2a, indocyanine green, and zinc phthalocyanine were used (FIG. 11). Although AlPcS2a has been used in many studies regarding photochemical internalization, the absorption maximum thereof is in a visible light region, and also, the singlet oxygen quantum yield thereof is low (0.17). Indocyanine green (ICG) is a photosensitizer used in photo dynamic therapy, photoacoustic imaging or the like. Indocyanine green has its absorption maximum in a near infrared region, but the singlet oxygen quantum yield thereof is low (0.12). Zinc phthalocyanine (ZnPc) is unsubstituted phthalocyanine having zinc in the center thereof, as with PS1. Zinc phthalocyanine has its absorption maximum in a visible light region, but the singlet oxygen quantum yield thereof is high.

Using these photosensitizers, a cell experiment involving the combined use of addition of the immunotoxin and PCI was carried out. As a result, a significant reduction in the cell viability was observed only in the cells, on which PCI was carried out using PS1 (FIG. 12). This is considered because photosensitization could not be performed on AlPcS2a and ZnPc using a near infrared light since the absorption maximum of AlPcS2a and ZnPc was in a visible light region; and also because ICG having its absorption maximum in a near infrared region could not release a sufficient amount of singlet oxygen because ICG had a low singlet oxygen quantum yield. From these results, it can be considered that PS1 is a photosensitizer that is superior to conventional photosensitizers under near infrared light irradiation.

<Verification of Photochemical Internalization (PCI)>

According to the previous experiments, the cytotoxicity of the immunotoxin could be improved by using PS1 in combination with near infrared light irradiation.

The currently proposed mechanisms of PCI are as follows:

1) an immunotoxin and a photosensitizer are together incorporated into cells due to endocytosis,
2) by irradiation with a near infrared light, singlet oxygen is generated by the action of the photosensitizer, and the endosomal membrane is damaged thereby, and
3) the immunotoxin is released into the cytoplasm.

In order to prove the occurrence of PCI, it is adequate if it can be observed that an immunotoxin and PS1 are simultaneously present in the endosome, and that the immunotoxin is released into the cytoplasm after light irradiation. However, since the absorption maximum of PS1 is present in a near infrared region (775 nm), it is not suitable for excitation with a laser (633 nm) of a confocal laser microscope. In addition, the fluorescence quantum yield of PS1 is low (0.04). Accordingly, it is considered difficult to observe PS1 in cells. For these reasons, the release of the immunotoxin into the cytoplasm was observed by light irradiation. In order to observe the release of the immunotoxin into the cytoplasm, a fluorescein dye was utilized. Fluorescein has a property by which the fluorescence intensity of fluorescein increases under acidic conditions (M. M. Martin and L. Lindqvist, J. Lumin., 1975, 10, 381-390). By utilizing this property, the group of Otsuki et al. has shown the endosomal escape of a fluorescein-labeled shRNA, and has assumed that the membrane structure of the endosome is destabilized due to singlet oxygen generated by near infrared light irradiation, an increase in pH occurs in the endosome, the fluorescence intensity of fluorescein is thereby increased (T.

Otsuki et al., Sci. Rep., 2015, 5, 18577). As with this experiment, an antibody was labeled with fluorescein, and the endosomal escape of the antibody according to PCI was observed under a confocal microscope.

First, a biotinylated anti-EGFR antibody was mixed with streptavidin-FITC that was in an amount of 5 equivalents relative to the biotinylated anti-EGFR antibody, so as to obtain a fluorescein-labeled antibody. To A431 cells (60,000 cells/dish), the fluorescein-labeled antibody (1.2 nM) and PS1 (1 μM) were added, and the obtained mixture was then incubated for 24 hours. Thereafter, Hoechst33342 (75 nM) was added to the reaction mixture, and the thus obtained mixture was then incubated for 30 minutes. After that, the medium was removed. The residue was washed with PBS 4 times, a medium that did not contain phenol red was added, and the obtained mixture was then observed under a confocal microscope. The results was as shown in FIG. 13. The fluorescence intensity of fluorescein (green color) in the cells was not strong before the near infrared light irradiation, regardless of the presence or absence of PS1. It is considered that endosomal escape has already occurred in sites seen as dots, in which the fluorescence of fluorescein was strong.

Subsequently, near infrared light irradiation (13.8 mW/cm2 for 20 min, 16.6 J/cm2) was carried out, and the resultant was then observed under a confocal microscope again. The results was as shown in FIG. 14. An increase in the fluorescence intensity of fluorescein was observed only in the cells to which PS1 was added.

In order to quantitatively evaluate fluorescence intensity, the fluorescence of fluorescein per cell was quantified using ImageJ. The mean value of fluorescein-derived green fluorescence in the cell area was obtained, and the obtained value was then divided by the number of cells contained in the area, so as to obtain fluorescence intensity per cell. The number of cells was estimated based on the number of nuclei stained with Hoechst33342. The results of the quantification of the fluorescein fluorescence was as shown in FIG. 15. From these results, a significant increase in the fluorescence intensity was observed only in the cells on which addition of PS1 and irradiation with a near infrared light were carried out. Therefore, it is considered that the endosomal escape of the fluorescein-labeled antibody has occurred according to PCI using PS1.

<Cell Experiment Using EGFR-Expressing A549 Cells>

The same experiment as described above was carried out using A549 cells expressing EGFR at a low level. It has been reported that the A549 cells are human lung adenocarcinoma epithelial cells, and that the expression level of EGFR in the A549 cells is about 10% of the expression level of EGFR in the A431 cells (S. Derer et al., J. Immunol., 2012, 189, 5230-5239). There have been studies involving the use of an immunotoxin that targets EGFR on A549 cells (C. Deng et al., Oncotarget, 2017, 8, 38568-38580; and X. Zhou et al., J. Cancer Res. Clin. Oncol., 2012, 138, 1081-1090). However, possibly due to the low expression level of EGFR, there have been almost no study examples that could show sufficient cytotoxicity.

In order to examine the concentration of PS1 that does not have cytotoxicity only by PCI, only addition of PS1 and near infrared light irradiation were carried out on A549 cells. First, A549 cells (5,000 cells/well) were seeded on a 96-well plate, and 24 hours later, PS1 (0 to 20 μM) was added thereto. Eighteen hours later, the medium containing PS1 was removed, and the cells were then washed with PBS. After that, a new medium was added, and irradiation (6.1 mW/cm$^2$ for 60 min, 22 J/cm$^2$) with a near infrared light (700 to 1100 nm) was then carried out. Forty-eight hours after the irradiation, CCK-8 was added to the resultant, and the absorption at a wavelength of 450 nm was then measured using a plate reader, so that cell viability was measured (FIG. 16). As a result, it was found that 20 μM or less of PS1 does not have cytotoxicity, regardless of the presence or absence of near infrared light irradiation. Therefore, the optimal concentration of PS1 that does not exhibit cytotoxicity only by PCI is considered to be approximately 1 μM.

Subsequently, using an immunotoxin and PS1, an experiment of performing PCI on A549 cells was carried out. A549 cells (5,000 cells/well) were seeded on a 96-well plate, and 24 hours later, the immunotoxin (panitumumab-saporin, 0 to 4 nM) and PS1 (1 μM) were added thereto. Eighteen hours later, the medium containing the immunotoxin and PS1 was removed, and the cells were then washed with PBS. After that, a new medium was added, and irradiation (6.1 mW/cm$^2$ for 60 min, 22 J/cm$^2$) with a near infrared light (700 to 1100 nm) was then carried out. Forty-eight hours after the irradiation, CCK-8 was added to the resultant, and the absorption at a wavelength of 450 nm was then measured using a plate reader, so that cell viability was measured. The results was as shown in FIG. 17, and the cytotoxicity of the immunotoxin was significantly improved by the combined use of PCI. In addition, a reduction in the cell viability was not observed only by performing PCI with 1 μM PS1. From these results, it was suggested that an immunotoxin that targets a membrane protein that has not been conventionally targeted due to its low expression level would be likely to acquire cytotoxicity by the combined use of PCI.

<Cell Experiment Using EGFR-Non-Expressing HEK293T Cells>

Next, the same experiment as described above was carried out using HEK293T cells as EGFR-non-expressing cells. It has been reported that HEK293T cells are human embryonic kidney cell-derived cells, in which the expression level of EGFR is extremely low. First, in order to examine the concentration of PS1 that does not exhibit cytotoxicity only by PCI, only addition of PS1 and near infrared light irradiation were carried out on HEK293T cells.

First, HEK293T cells (10,000 cells/well) were seeded on a 96-well plate, and 24 hours later, PS1 (0 to 20 μM) was added thereto. Eighteen hours later, the medium containing PS1 was removed, and the cells were then washed with PBS. After that, a new medium was added, and irradiation (6.1 mW/cm$^2$ for 60 min, 22 J/cm$^2$) with a near infrared light (700 to 1100 nm) was then carried out. Forty-eight hours after the irradiation, CCK-8 was added to the resultant, and the absorption at a wavelength of 450 nm was then measured using a plate reader, so that cell viability was measured. The results was as shown in FIG. 18, and it was found that PS1 exhibits cytotoxicity as a result of near infrared light irradiation, when the PS1 is used in a concentration of 0.8 μM or more. Moreover, 20 μM PS1 has strong cytotoxicity, regardless of the presence or absence of near infrared light irradiation. This is considered because HEK293T cells incorporate more PS1 molecules therein than other cancer cells do, since the HEK293T has the property of easy transfection. Therefore, the optimal concentration of PS1 that does not exhibit cytotoxicity only by PCI is considered to be approximately 0.1 μM.

After examining the optimal concentration of PS1, using an immunotoxin and PS1, an experiment of performing PCI on HEK293T cells was carried out. HEK293T cells (10,000 cells/well) were seeded on a 96-well plate, and 24 hours later, the immunotoxin (panitumumab-saporin, 0 to 4 nM) and PS1 (0.1 μM) were added thereto. Eighteen hours later, the medium containing the immunotoxin and PS1 was removed, and the cells were then washed with PBS. After that, a new medium was added, and irradiation (6.1 mW/$cm^2$ for 60 min, 22 J/$cm^2$) with a near infrared light (700 to 1100 nm) was then carried out. Forty-eight hours after the irradiation, CCK-8 was added to the resultant, and the absorption at a wavelength of 450 nm was then measured using a plate reader, so that cell viability was measured. The results was as shown in FIG. 19. A clear reduction in the cell viability was not observed by either the single use of the immunotoxin, or the combined use of the immunotoxin and PCI. From these results, it was found that the anti-EGFR immunotoxin exhibits only to cells that express EGFR, even though PCI is used in combination with the immunotoxin.

<Measurement of Membrane-Damaging Ability of PS1 (Zn6PTPc)>

In order to examine whether a lipid membrane can be destroyed by irradiation of PS1 (Zn6PTPc) with a near infrared light, a hemolytic assay was carried out using erythrocytes. The hemolytic assay is a method of examining the degree of hemolysis by quantifying the amount of hemoglobin released to the outside of erythrocytes as a result of the hemolysis.

First, blood collected from mice was centrifuged at 5000 g for 5 minutes to obtain blood cell components. The washing of the precipitate (30 µl) with PBS at 5000 g for 4 minutes was repeated 5 times. Thereafter, a supernatant was then discarded, and the residue was diluted with 550 µl. After that, 20 µl of the erythrocyte solution and 80 µl of a PBS solution containing PS1 (Zn6PTPc) (final Zn6PTPc concentration: 0.1, 1, 10, or 100 µM) were added to a 96-well plate. On the other hand, PBS that did not contain PS1 (Zn6PTPc) was used as a negative control, and Milli-Q was used as a positive control. Incubation was carried out at 37° C. for 100 minutes, and irradiation (6.1 mW/$cm^2$ for 60 min, 22 J/$cm^2$) with a near infrared light (700 to 1100 nm) was then carried out. Thereafter, incubation was further carried out at 37° C. for 2 hours, and the solution in each well was then recovered, and was then centrifuged at 5000 g for 4 minutes. The supernatant was transferred in an amount of 70 µl each to a novel 96-well plate. The absorption at 541 nm was measured using a plate reader, so that the amount of hemoglobin released into the supernatant was measured. The results was as shown in FIG. 20, and it was fond that hemolysis is promoted by light irradiation, and that the degree of the hemolysis increases together with an increase in the concentration of PS1 (Zn6PTPc). On the other hand, it was found that, when light irradiation is not carried out, hemolysis does not take place, regardless of the concentration of PS1 (Zn6PTPc).

<Cell Staining with Annexin PI>

A431 cells (100,000 cells/well) were seeded on a 12-well plate, and 24 hours later, an immunotoxin (panitumumab-saporin) (160 pM) and PS1 (Zn6PTPc) (0.1, 1, or 10 µM) were added thereto. Eighteen hours later, the medium containing the immunotoxin and PS1 (Zn6PTPc) was removed, and the cells were then washed with DMEM. Thereafter, a new medium was added to the resulting cells, and irradiation (9.9 mW/$cm^2$ for 37 min, 22 J/$cm^2$) with a near infrared light (700 to 1100 nm) was then carried out. Forty-eight hours after the light irradiation, the cells were stained in accordance with the protocols of Annexin V-FITC/PI Kit, and the fluorescence intensity was then measured by flow cytometry.

The measurement was carried out until the number of cells in the R1 gate reached 10000. The results was as shown in FIG. 21. As shown in FIG. 21(*a*), together with an increase in the PS1 (Zn6PTPc) concentration, the number of cells in the gate decreased, and the points around the origin increased. This is considered because dead cells were shattered and thus, the cells could not retain their original size. In addition, as shown in FIG. 21(*c*), it is found that the point group is shifted to the upper right portion, together with an increase in the PS1 (Zn6PTPc) concentration. The cell death stained with both annexin and PI is apoptosis. Thus, it was demonstrated that, in the present PCI, apoptosis was induced by inactivation of the ribosome with saporin, as hypothesized.

<Cancer-Bearing Mouse Experiment (A549)>

An experiment was carried out using eight 6-week-old nude mice. A549 ($4\times10^6$ cells/mouse) was transplanted into the subcutis of the right thigh of each mouse. On the day in which the tumor volume reached 100 $mm^3$ (Day 0), the 8 mice were randomly divided into 4 groups (group A: control; group B: 2.5 mg/kg PS1 (Zn6PTPc); group C: 5.0 mg/kg PS1 (Zn6PTPc); and group D: 2.5 mg/kg PS1 (Zn6PTPc)+0.3 mg/kg IT). In groups A, B, and C, 100 µl of PBS was injected into the vein of the tail portion of each mouse. In group D, 100 µl of an immunotoxin (panitumumab-saporin) adjusted to 0.3 mg/kg was injected into the vein of the tail portion of each mouse. Two days after the injection (Day 2), in group A, 100 µl (in serum, containing 22% DMF) of PBS was injected into the subcutis of the tumor portion of each mouse, and in groups B and D, 100 µl of 2.5 mg/kg PS1 (Zn6PTPc) was injected into the subcutis of the tumor portion of each mouse. In group C, 100 µl of 5.0 mg/kg PS1 (Zn6PTPc) was injected into the subcutis of the tumor portion of each mouse. Further, 3 hours after the injection, the mice were irradiated (22 J/$cm^2$) with a near infrared light (700 to 1100 nm).

The results are shown in FIG. 22.

The maximum cross section of the tumor is 5×3 mm. There are no granulation tissues in the tumor. Formation of thick membranous granulation tissues is observed in the tumor margin. 50% Of the tumor region falls in geographic coagulative necrosis. 20% Of the tumor region consists of tumor cells inclined to nuclear enrichment, fragmentation, disintegration of a cell nucleus, or disintegration consisting of nuclear fragments. The remaining 30% consists of viable tumor cells.

The invention claimed is:

1. A compound represented by the following formula (1) or a salt thereof:

[Formula 1]

(1)

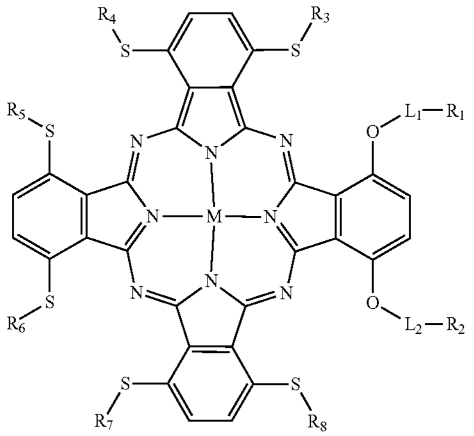

wherein $L_1$ and $L_2$ each independently represent a single bond, —O—, —CO—, an alkylene group containing 1 to 8 carbon atoms, a sugar chain, or a combination thereof; $R_1$ and $R_2$ each independently represent an alkyl group containing 1 to 8 carbon atoms, a carboxylic acid group, an amino group, a hydroxyl group, a thiol group, or a biotin residue; $R_3$, $R_4$, $R_5$, $R_6$, $R_7$ and $R_8$ each independently represent an alkyl group containing 1 to 8 carbon atoms, a phenyl group, a carboxylic acid group, an amino group, a hydroxyl group, a thiol group, or a biotin residue; and M represents Mg, Zn, Fe, P, Si, Cu, Sn, Al, Ti, Mo, or Ni.

2. The compound according to claim 1 or a salt thereof, wherein $L_1$ and $L_2$ each independently represent an alkylene group containing 1 to 8 carbon atoms.

3. The compound according to claim 1 or a salt thereof, wherein $R_1$ and $R_2$ each represent a carboxylic acid group.

4. The compound according to claim 1 or a salt thereof, wherein $R_3$, $R_4$, $R_5$, $R_6$, $R_7$, and $R_8$ each represent a phenyl group.

5. The compound according to claim 1 or a salt thereof, wherein M represents Zn.

6. A medicament for killing tumor cells, comprising the compound according to claim 1 or a salt thereof.

7. A method comprising:

(1) allowing the compound according to claim 1 or a salt thereof to come into contact with tumor cells; and (2) killing the tumor cells by irradiating the cells with a wavelength that is effective for activating the compound or a salt thereof.

8. A medicament for killing tumor cells, comprising:

(a) the compound according to claim 1 or a salt thereof; and (b) a low-molecular-weight antitumor agent.

9. A method comprising:

(1) allowing the compound according to claim 1 or a salt thereof and a low-molecular-weight antitumor agent to come into contact with tumor cells; and then, (2) a step of killing the tumor cells by irradiating the cells with a wavelength that is effective for activating the compound or a salt thereof.

10. A medicament for killing tumor cells, comprising:

(a) the compound according to claim 1 or a salt thereof; and (b) a conjugate of a substance that binds to a target substance on the surface of tumor cells and a cytotoxin.

11. The medicament according to claim 10, wherein the substance that binds to a target substance on the surface of tumor cells is a conjugate of an antibody or a fragment thereof, a ligand or a peptide, and a cytotoxin.

12. The medicament according to claim 11, wherein the antibody is an antibody reacting against Epidermal Growth Factor Receptor (EGFR, ERBB1, ERBB2, ERBB3, or ERBB4), Mesothelin, Ephrin type-A receptor 2 (EphA2), Glypican3 (GPC3), Cadherin17 (CDH17), Cadherin3 (CDH3), or Roundabout homolog 1 (Robo1).

13. The medicament according to claim 10, wherein the cytotoxin is saporin, gelonin, or *Pseudomonas* exotoxin.

14. A method comprising:

(1) allowing the compound according to claim 1 or a salt thereof and a conjugate to come into contact with tumor cells, wherein the conjugate is a conjugate of a substance that binds to a target substance on a surface of the tumor cells and a cytotoxin; and then, (2) killing the tumor cells by irradiating the cells with a wavelength that is effective for activating the compound or a salt thereof.

15. The method according to claim 7, wherein the tumor cells are cancer cells of any one of head and neck cancer, lung cancer, liver cancer, colorectal cancer, skin cancer, esophageal cancer, stomach cancer, cervical cancer, endometrial cancer, mesothelioma, brain tumor, malignant melanoma, breast cancer, bile duct cancer, pancreatic cancer, ovarian cancer, kidney cancer, bladder cancer, prostate cancer, malignant lymphoma, and osteosarcoma.

* * * * *